United States Patent
Nagata et al.

(10) Patent No.: US 12,233,796 B2
(45) Date of Patent: Feb. 25, 2025

(54) CONTROL DEVICE AND CONTROL METHOD FOR ADJUSTMENT OF VEHICLE DEVICE

(71) Applicant: Sony Corporation, Tokyo (JP)

(72) Inventors: Koji Nagata, Tokyo (JP); Takashi Saitoh, Tokyo (JP); Kenichiro Watanabe, Tokyo (JP)

(73) Assignee: SONY CORPORATION, Tokyo (JP)

( * ) Notice: Subject to any disclaimer, the term of this patent is extended or adjusted under 35 U.S.C. 154(b) by 1001 days.

(21) Appl. No.: 17/044,382

(22) PCT Filed: May 27, 2019

(86) PCT No.: PCT/JP2019/020807
§ 371 (c)(1),
(2) Date: Oct. 1, 2020

(87) PCT Pub. No.: WO2019/235274
PCT Pub. Date: Dec. 12, 2019

(65) Prior Publication Data
US 2021/0101547 A1    Apr. 8, 2021

(30) Foreign Application Priority Data
Jun. 7, 2018   (JP) ................................ 2018-109696

(51) Int. Cl.
*B60R 16/037*   (2006.01)
*A61B 5/00*   (2006.01)
(Continued)

(52) U.S. Cl.
CPC .......... *B60R 16/037* (2013.01); *A61B 5/1116* (2013.01); *A61B 5/18* (2013.01);
(Continued)

(58) Field of Classification Search
CPC ....... A61B 5/1116; A61B 5/18; A61B 5/6893; B60K 35/00; B60N 2/002; G06F 3/017
See application file for complete search history.

(56) References Cited

U.S. PATENT DOCUMENTS 5,848,661 A * 12/1998 Fu ..................... B60N 2/002
                                                       297/410
6,055,473 A *  4/2000 Zwolinski .......... G01G 19/4142
                                                       701/45
(Continued)

FOREIGN PATENT DOCUMENTS

JP    08-052036 A    2/1996
JP    11-326084 A    11/1999
(Continued)

OTHER PUBLICATIONS

International Search Report and Written Opinion mailed on Aug. 13, 2019 for PCT/JP2019/020807 filed on May 27, 2019, 10 pages including English Translation of the International Search Report.

*Primary Examiner* — Ramsey Refai
(74) *Attorney, Agent, or Firm* — XSENSUS LLP

(57) ABSTRACT

The present disclosure relates to a control device, a control method, a program, and a mobile object which are capable of improving convenience. Pressure distributions for a plurality of measurement ranges of a seat on which a user is seated, and time variations of the pressure distributions are measured, and operation of a device or the seat is controlled according to the measurement result. Furthermore, it is determined that a behavior of the user is a gesture for a predetermined operation input, and control according to the gesture is performed. At this time, it is determined whether it is a gesture of the user intended to be the operation input or a posture change of the user not intended to be the operation input. The present technique is applicable to, for (Continued)

example, a control processing device that performs control processing for a seat for vehicle.

17 Claims, 32 Drawing Sheets

(51) Int. Cl.
| | |
|---|---|
| *A61B 5/11* | (2006.01) |
| *A61B 5/18* | (2006.01) |
| *B60K 35/00* | (2006.01) |
| *B60N 2/00* | (2006.01) |
| *B60N 2/02* | (2006.01) |
| *G06F 3/01* | (2006.01) |
| *B60K 35/10* | (2024.01) |
| *B60K 35/26* | (2024.01) |

(52) U.S. Cl.
CPC ............ *A61B 5/6893* (2013.01); *B60K 35/00* (2013.01); *B60N 2/0022* (2023.08); *B60N 2/0023* (2023.08); *B60N 2/0239* (2023.08); *G06F 3/017* (2013.01); *B60K 35/10* (2024.01); *B60K 35/26* (2024.01); *B60K 2360/146* (2024.01); *B60N 2210/40* (2023.08); *B60N 2220/20* (2023.08)

(56) References Cited

U.S. PATENT DOCUMENTS

| | | | | |
|---|---|---|---|---|
| 6,327,917 | B1* | 12/2001 | Nitschke | ........... B60R 21/01556 |
| | | | | 177/144 |
| 6,402,195 | B1* | 6/2002 | Eisenmann | ............ B60N 2/809 |
| | | | | 297/410 |
| 7,481,493 | B2* | 1/2009 | Fujita | ........................ B60N 2/72 |
| | | | | 297/452.56 |
| 7,967,377 | B2* | 6/2011 | Truckenbrodt | ........ B60N 2/002 |
| | | | | 297/410 |
| 2002/0167486 | A1* | 11/2002 | Tan | ........................ A61B 5/1116 |
| | | | | 345/156 |
| 2007/0152483 | A1* | 7/2007 | Fujita | ........................ B60N 2/72 |
| | | | | 297/284.1 |
| 2011/0178680 | A1* | 7/2011 | Kato | ................. B60W 50/0097 |
| | | | | 701/1 |
| 2014/0309871 | A1* | 10/2014 | Ricci | ..................... G06Q 30/012 |
| | | | | 701/36 |
| 2015/0131857 | A1* | 5/2015 | Han | ...................... G06V 20/597 |
| | | | | 382/103 |
| 2016/0103499 | A1 | 4/2016 | Yamamoto | |

FOREIGN PATENT DOCUMENTS

| | | |
|---|---|---|
| JP | 2008-195323 A | 8/2008 |
| JP | 2011-053986 A | 3/2011 |
| JP | 2011-164825 A | 8/2011 |
| JP | 2016509327 A | 3/2016 |
| JP | 2017-502865 A | 1/2017 |
| JP | 2017-065504 A | 4/2017 |
| JP | 2017-087752 A | 5/2017 |
| WO | 2011/030491 A1 | 3/2011 |
| WO | 2016/167331 A1 | 10/2016 |
| WO | 2018/096913 A1 | 5/2018 |

\* cited by examiner

Fig. 6

LOAD MEASUREMENT VALUE

A

| 0 | 0 | 0 | 0 | 0 | 0 | 0 |
|---|---|---|---|---|---|---|
| 0 | 9 | 12 | 7 | 3 | 2 | 0 |
| 0 | 12 | 30 | 56 | 32 | 5 | 0 |
| 11 | 35 | 98 | 80 | 47 | 6 | 5 |
| 8 | 23 | 88 | 78 | 15 | 8 | 0 |
| 0 | 14 | 25 | 11 | 13 | 10 | 2 |
| 0 | 0 | 10 | 7 | 4 | 3 | 0 |

LOAD DISTRIBUTION SHAPE

B

| 0 | 0 | 0 | 0 | 0 | 0 | 0 |
|---|---|---|---|---|---|---|
| 0 | 1 | 1 | 1 | 0 | 0 | 0 |
| 0 | 1 | 1 | 1 | 1 | 1 | 0 |
| 1 | 1 | 1 | 1 | 1 | 1 | 1 |
| 1 | 1 | 1 | 1 | 1 | 1 | 0 |
| 0 | 1 | 1 | 1 | 1 | 1 | 0 |
| 0 | 0 | 1 | 1 | 0 | 0 | 0 |

LOAD AREA DISTRIBUTION

C

| 0 | 0 | 0 | 0 | 0 | 0 | 0 |
|---|---|---|---|---|---|---|
| 0 | A22 | A32 | A42 | 0 | 0 | 0 |
| 0 | A23 | A33 | A43 | A53 | A63 | 0 |
| A14 | A24 | A34 | A44 | A54 | A64 | A74 |
| A15 | A25 | A35 | A45 | A55 | A65 | 0 |
| 0 | A26 | A36 | A46 | A56 | A66 | 0 |
| 0 | 0 | A37 | A47 | 0 | 0 | 0 |

Fig. 7

| | 1 | 2 | 3 | 4 | 5 | .... | n |
|---|---|---|---|---|---|---|---|
| | \multicolumn{7}{l|}{PHYSICAL AREA TABLE OF PRESSURE SENSORS: UNIT [mm]} |
| 1 | A11 | A21 | A31 | A41 | A51 | ... | An1 |
| 2 | A12 | A22 | A32 | A42 | A52 | ... | An2 |
| 3 | A13 | A23 | A33 | A43 | A53 | ... | An3 |
| ... | ... | ... | ... | ... | ... | ... | ... |
| m | A1m | A2m | A3m | A4m | A5m | ... | Anm |

Fig. 10

| | SHORT-TERM SECTION AVERAGE | SHORT-TERM SECTION VARIANCE |
|---|---|---|
| SUM | $SAve\_Wsum(t) = \frac{1}{S+1} \sum_{i=t}^{t-s} Wsum(i)$ | $SS2\_Wsum(t) = \frac{1}{S+1} \sum_{i=t}^{t-s} (Wsum(i) - SAve\_Wsum(t))^2$ |
| CENTROID COORDINATES | $[SAve\_Cx(t), SAve\_Cy(t)] = \left[ \frac{1}{S+1} \sum_{i=t}^{t-s} Cx(i), \frac{1}{S+1} \sum_{i=t}^{t-s} Cy(i) \right]$ | $[SS2\_Cx(t), SS2\_Cy(t)] = \left[ \frac{1}{S+1} \sum_{i=t}^{t-s} (Cx(i), -SAve\_Cx(t)), \frac{1}{S+1} \sum_{i=t}^{t-s} (Cy(i), -SAve\_Cy(t)) \right]$ |

Fig. 11

| | LONG-TERM SECTION AVERAGE | LONG-TERM SECTION VARIANCE |
|---|---|---|
| SUM | $LAve\_Wsum(t) = \frac{1}{L+1}\sum_{i=t}^{t-L} Wsum(i)$ | $LS2\_Wsum(t) = \frac{1}{L+1}\sum_{i=t}^{t-L}(Wsum(i) - LAve\_Wsum(t))^2$ |
| CENTROID COORDINATES | $[LAve\_Cx(t), LAve\_Cy(t)] = \left[\frac{1}{L+1}\sum_{i=t}^{t-L} Cx(t), \frac{1}{L+1}\sum_{i=t}^{t-L} Cy(t)\right]$ | $[LS2\_Cx(t), LS2\_Cy(t)] = \left[\frac{1}{L+1}\sum_{i=t}^{t-L}(Cx(i), -LAve\_Cx(t)), \frac{1}{L+1}\sum_{i=t}^{t-L}(Cy(i), -LAve\_Cy(t))\right]$ |

Fig. 28

| | OPERATION OUTPUT | GESTURE IMAGE | DETERMINATION CONDITIONS | STOP CONDITIONS |
|---|---|---|---|---|
| ① | RECLINE SEATBACK (BACKREST) *FOOTREST RAISED IN CONJUNCTION | ACTION OF PUSHING THE BACKREST ONLY BY THE SHOULDER WITH THROWING OUT THE CHEST FROM THE STATE OF POSTURE ADJUSTED AND LEANING AGAINST THE BACKREST RECLINES THE BACKREST. RETURNING THE SHOULDER BACK STOPS THE MOVEMENT OF THE BACKREST. | WHEN THE Y COORDINATE ($C_y\_BR$) OF THE BACKREST CENTROID MAINTAINS A VALUE LARGER THAN COND_BR_UP FOR A TIME LONGER THAN THE SHORT-TERM EVALUATION PERIOD, ON THE BASIS OF THE VALUE AT THE DETERMINATION FOR TRANSITION TO THE GESTURE WAITING STATE. | IT BECOMES A VALUE SMALLER THAN COND_BR_RECLINE, OR IT REACHES THE MAXIMUM ANGLE. |
| | RAISE SEATBACK (BACKREST) *FOOTREST LOWERED IN CONJUNCTION | ACTION OF THE SHOULDER LEAVING THE BACKREST FROM THE STATE OF POSTURE ADJUSTED AND LEANING AGAINST THE BACKREST. RETURNING THE BACKREST RAISES THE BACKREST. RETURNING THE SHOULDER BACK STOPS THE MOVEMENT OF THE BACKREST. | WHEN THE Y COORDINATE ($C_y\_BR$) OF THE BACKREST CENTROID MAINTAINS A VALUE SMALLER THAN COND_BR_DOWN FOR A TIME LONGER THAN THE SHORT-TERM EVALUATION PERIOD, ON THE BASIS OF THE VALUE AT THE DETERMINATION FOR TRANSITION TO THE GESTURE WAITING STATE. | IT BECOMES A VALUE LARGER THAN COND_BR_RETURN, OR IT REACHES THE MINIMUM ANGLE. |
| ② | RAISE FOOTREST | ① KNOCKING ON THE FOOTREST WITH THE HEEL RAISES THE FOOTREST, KNOCKING AGAIN STOPS IT. ② SLIGHTLY RAISE ONE OR BOTH LEGS. PUTTING THE LEGS ON THE FOOTREST STOPS IT. | WHEN THE Y COORDINATE ($C_y\_FR$) OF THE CENTROID OF EITHER THE LEFT OR RIGHT FOOTREST MAINTAINS A VALUE LARGER THAN COND_FR_UP FOR A TIME LONGER THAN THE SHORT-TERM EVALUATION PERIOD. | IT BECOMES A VALUE SMALLER THAN COND_FR_UP, OR IT REACHES THE MAXIMUM ANGLE. |
| | LOWER FOOTREST | PUSHING DOWN FIRMLY ON THE BOTTOM OF THE FOOTREST LOWERS IT. STOPPING THE PUSHING STOPS IT. | WHEN THE Y COORDINATE ($C_y\_FR$) OF THE CENTROID OF EITHER THE LEFT OR RIGHT FOOTREST MAINTAINS A VALUE SMALLER THAN COND_FR_DOWN FOR A TIME LONGER THAN THE SHORT-TERM EVALUATION PERIOD. | IT BECOMES A VALUE LARGER THAN COND_FR_UP, OR IT REACHES THE MINIMUM ANGLE. |
| ③ | MOVE SEAT FORWARD | MOVING THE HIPS FORWARD ON THE SEAT SURFACE MOVES THE SEAT FORWARD. RETURNING BACK STOPS IT. | WHEN THE Y COORDINATE ($C_y\_SE$) OF THE SEAT CENTROID MAINTAINS A VALUE SMALLER THAN COND_SE_FORWARD FOR A TIME LONGER THAN THE SHORT-TERM EVALUATION PERIOD, ON THE BASIS OF THE VALUE AT THE DETERMINATION FOR TRANSITION TO THE GESTURE WAITING STATE. | IT BECOMES A VALUE SMALLER THAN COND_SE_FWD, OR IT REACHES THE MAXIMUM ANGLE. |
| | MOVE SEAT BACKWARD | MOVING THE HIPS BACKWARD ON THE SEAT SURFACE MOVES THE SEAT BACKWARD. RETURNING BACK STOPS IT. | WHEN THE Y COORDINATE ($C_y\_SE$) OF THE SEAT CENTROID MAINTAINS A VALUE SMALLER THAN COND_SE_BACKWARD FOR A TIME LONGER THAN THE SHORT-TERM EVALUATION PERIOD, ON THE BASIS OF THE VALUE AT THE DETERMINATION FOR TRANSITION TO THE GESTURE WAITING STATE. | IT BECOMES A VALUE LARGER THAN COND_SE_BWD, OR IT REACHES THE MINIMUM ANGLE. |

CONTROL DEVICE AND CONTROL METHOD FOR ADJUSTMENT OF VEHICLE DEVICE

CROSS-REFERENCE TO RELATED APPLICATIONS

The present application is based on PCT filing PCT/JP2019/020807, filed May 27, 2019, which claims priority to JP 2018-109696, filed Jun. 7, 2018, the entire contents of each are incorporated herein by reference.

TECHNICAL FIELD

The present disclosure relates to a control device, a control method, a program, and a mobile object, and particularly to a control device, a control method, a program, and a mobile object which are capable of improving convenience.

BACKGROUND ART

Techniques are being developed for adjusting the front and back positions of a driver seat according to a pressure value detected by a pressure sensor attached to the seat for vehicle, and for adjusting the seating state to provide better comfort based on the passenger's biological information acquired.

For example, PTL 1 describes a technique for detecting a reclining instruction signal by a pressure sensor attached to a seat for vehicle so that the reclining operation speed can be changed according to the detected signal.

CITATION LIST

Patent Literature

[PTL 1] Japanese Patent Application Publication No. H08-52036

SUMMARY

Technical Problem

As described above, techniques have been developed that use a pressure sensor attached to a seat for vehicle as an input. On the other hand, there is a need for capturing an occupant's conscious or unconscious behavior as an input and providing a function corresponding to the input, thereby improving convenience.

The present disclosure has been made in view of such circumstances, and an aim of the disclosure is to make it possible to further improve convenience.

Solution to Problem

A control device according to one aspect of the present disclosure includes a measurement unit that measures pressure distributions for a plurality of measurement ranges of a seat on which a user is seated, and time variations of the pressure distributions; and a control unit that controls operation of a device according to a measurement result from the measurement unit.

A control method according to one aspect of the present disclosure includes measuring pressure distributions for a plurality of measurement ranges of a seat on which a user is seated, and time variations of the pressure distributions; and controlling operation of a device according to a measurement result from the measuring.

A control method according to one aspect of the present disclosure includes measuring pressure distributions for a plurality of measurement ranges of a seat on which a user is seated, and time variations of the pressure distributions; and controlling a device according to a measurement result from the measuring.

A mobile object according to one aspect of the present disclosure is a mobile object provided with a seat on which a user is seated, and includes a measurement unit that measures pressure distributions for a plurality of measurement ranges of the seat, and time variations of the pressure distributions; and a control unit that controls operation of a device according to a measurement result from the measurement unit.

According to one aspect of the present disclosure, pressure distributions for a plurality of measurement ranges of a seat on which a user is seated, and time variations of the pressure distributions are measured, and operation of a device is controlled according to the measurement result.

Advantageous Effects of Invention

According to one aspect of the present disclosure, it is possible to improve convenience.

Note that the advantageous effect described here is not necessarily limited, and any advantageous effects described in the present disclosure may be enjoyed.

BRIEF DESCRIPTION OF DRAWINGS

FIG. 6 illustrates examples of a load distribution shape and a load area distribution.

FIG. 7 illustrates an example of a physical area table of the pressure sensor.

FIG. 10 illustrates examples of calculation of sums and centroid coordinates in terms of the sums and the centroid coordinates in short-term sections.

FIG. 11 illustrates examples of calculation of sums and centroid coordinates in terms of the sums and the centroid coordinates in long-term sections.

FIG. 28 illustrates examples of gesture and operation output.

DESCRIPTION OF EMBODIMENTS

Hereinafter, specific embodiments to which the present technique is applied will be described in detail with reference to the drawings.

<Configuration Example of Seat Control Processing Device>

Figure 1:
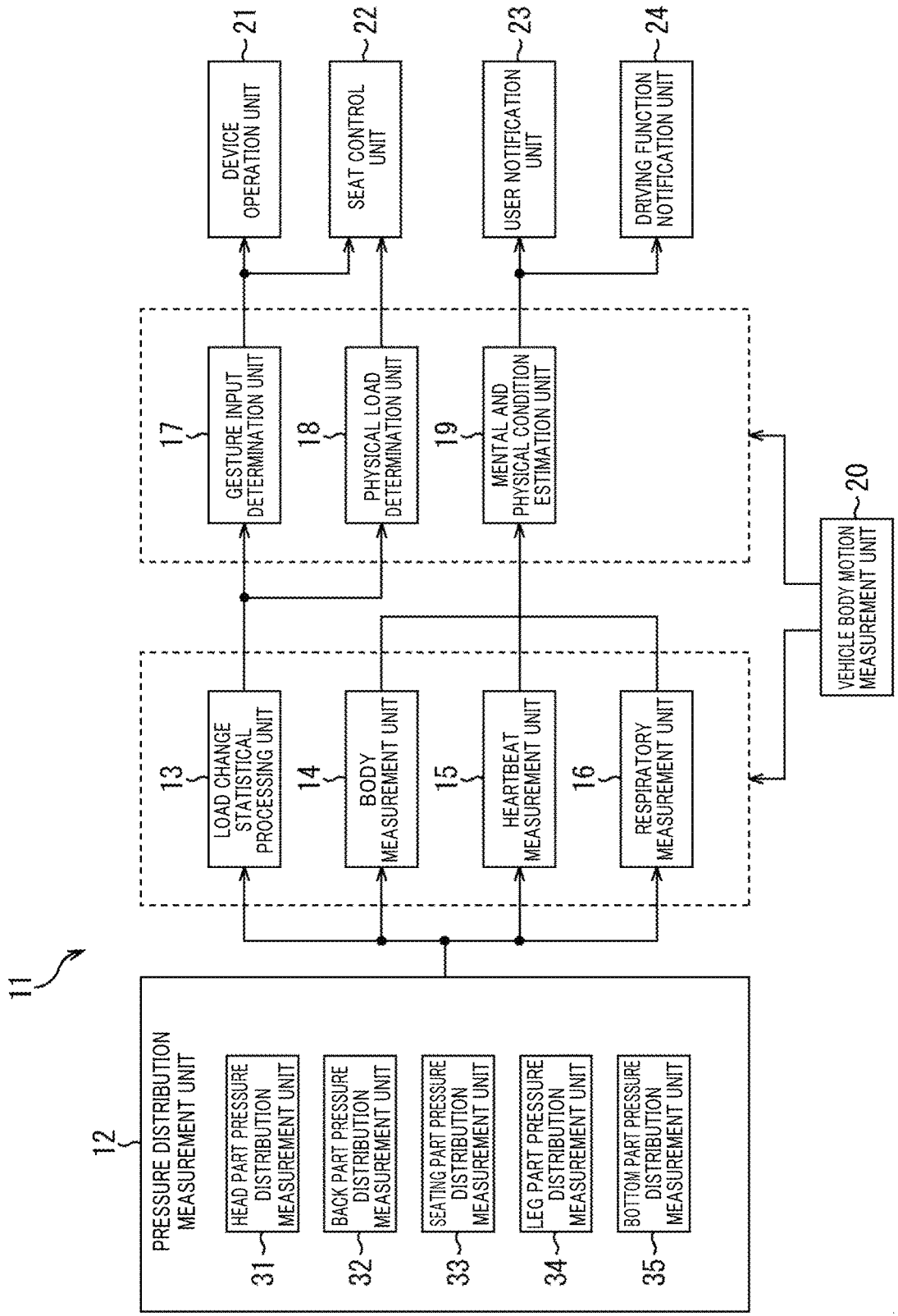
FIG. 1 is a block diagram illustrating a configuration example of one embodiment of a control processing device to which the present technique is applied.

FIG. 1 is a block diagram illustrating a configuration example of one embodiment of a control processing device for a seat for vehicle to which the present technique is applied.

As illustrated in FIG. 1, a control processing device 11 includes a pressure distribution measurement unit 12, a load change statistical processing unit 13, a body measurement unit 14, a heartbeat measurement unit 15, a respiration measurement unit 16, a gesture input determination unit 17, a body load determination unit 18, a mental and physical condition estimation unit 19, a vehicle body motion measurement unit 20, a device operation unit 21, a seat control unit 22, a user notification unit 23, and a driving function notification unit 24.

Figure 2:
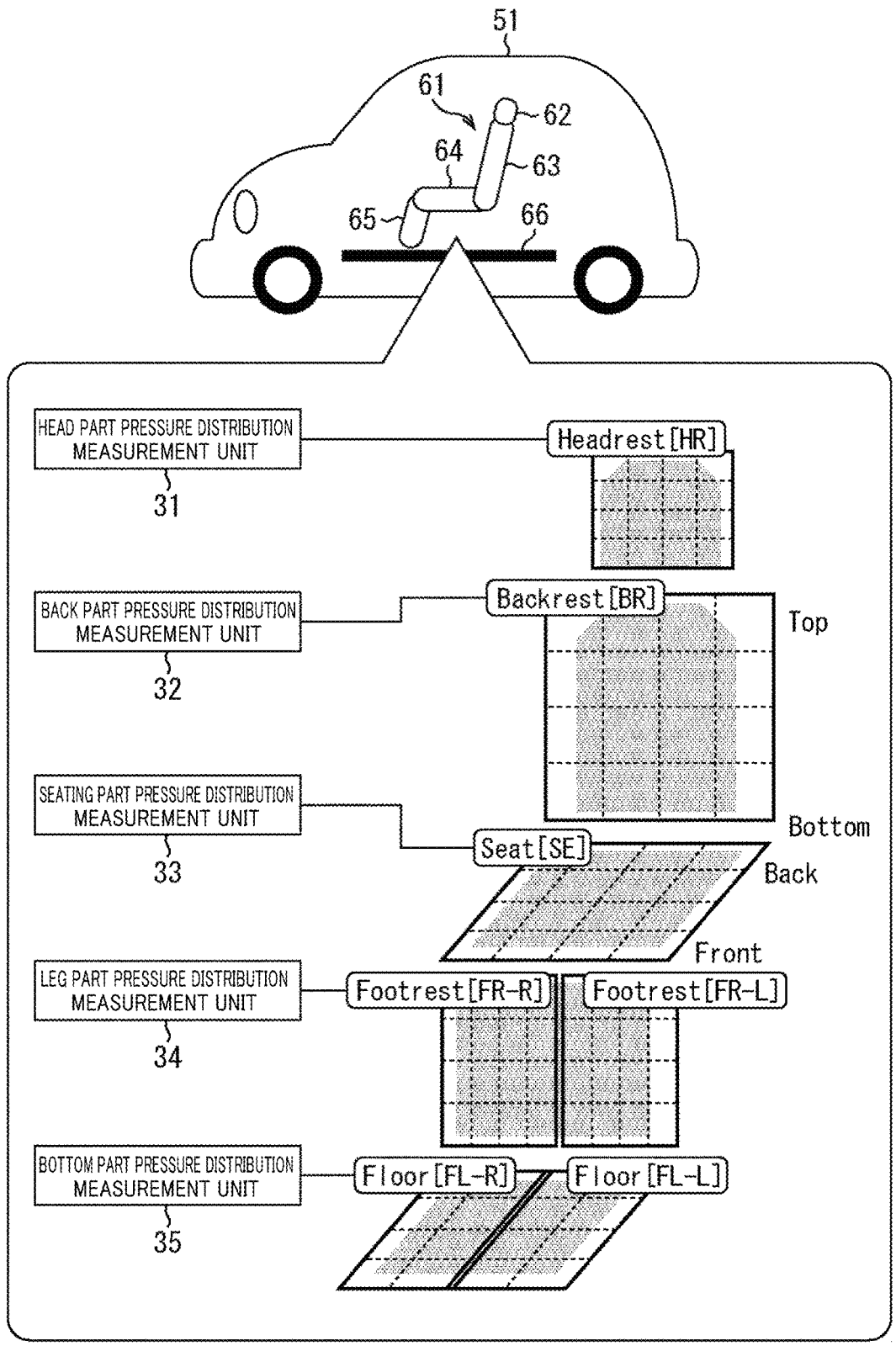
FIG. 2 is a diagram for explaining measurement ranges set for a seat of a vehicle.

For example, the control processing device 11 can use a load change in a seat 61 for seating an occupant such as a driver or a passenger in a vehicle 51 as illustrated in FIG. 2, which is caused by the behavior of the occupant to control a movable part of the seat 61 so as to improve comfortability. For example, the seat 61 includes movable parts such as a headrest part 62, a backrest part 63, a seat surface part 64, and a footrest part 65, and is fixed to a floor 66 of the vehicle 51.

The pressure distribution measurement unit 12 measures, for example, distributions of pressures applied to a plurality of measurement ranges set on the seat 61 by an occupant seated on the seat 61, and also measures time variations of the pressure distributions. Then, the pressure distribution measurement unit 12 supplies pressure distribution data obtained by measuring the pressure distributions and the time variations to the load change statistical processing unit 13, the body measurement unit 14, the heartbeat measurement unit 15, and the respiration measurement unit 16. In the example illustrated in FIG. 1, the pressure distribution measurement unit 12 includes a head part pressure distribution measurement unit 31, a back part pressure distribution measurement unit 32, a seating part pressure distribution measurement unit 33, a leg part pressure distribution measurement unit 34, and a bottom part pressure distribution measurement unit 35.

For example, regions indicated by gray hatching in FIG. 2 is set as measurement ranges, and the head part pressure distribution measurement unit 31 measures the distribution of pressure applied to the measurement range set for the headrest part 62. Similarly, the back part pressure distribution measurement unit 32 measures the distribution of pressure applied to the measurement range set for the backrest part 63, and the seating part pressure distribution measurement unit 33 measures the distribution of pressure applied to the measurement range set for the seat surface part 64. Further, the leg part pressure distribution measurement unit 34 measures the distribution of pressure applied to the right and left measurement ranges set for the footrest part 65. Furthermore, the bottom part pressure distribution measurement unit 35 measures the distribution of pressure applied to the right and left measurement ranges set for a foot region in the vicinity of the bottom of the seat 61 (in front of the footrest part 65) on the floor 66 of the vehicle 51.

The load change statistical processing unit 13 performs statistical processing of load changes according to the behavior of an occupant on the pressure distribution data of each measurement range supplied from the pressure distribution measurement unit 12, and thus acquires, for example, various types of average values and variance values, which will be described below. Then, the load change statistical processing unit 13 supplies the statistically processed pressure distribution data subjected to the statistical processing to the gesture input determination unit 17 and the body load determination unit 18.

The body measurement unit 14, the heartbeat measurement unit 15, and the respiration measurement unit 16 each perform measurement based on the pressure distribution data supplied from the pressure distribution measurement unit 12, acquires the body data, heartbeat data, and respiration data of an occupant seated on the seat 61, and supplies them to the mental and physical condition estimation unit 19. For example, the body measurement unit 14 can measure the weight and body balance, gestures, and the like of the occupant to acquire them as body data, the heartbeat measurement unit 15 can acquire heartbeat data from pressure changes in the thigh of the occupant, and the respiration measurement unit 16 can acquire respiration data from pressure changes in the chest of the occupant.

The gesture input determination unit 17 determines whether or not the behavior of the occupant seated on the seat 61 is a gesture for performing an operation input, based on the statistically processed pressure distribution data supplied from the load change statistical processing unit 13. At this time, the gesture input determination unit 17 can determine whether the behavior of the occupant is a gesture intended to be an operation input or a posture change not intended to be an operation input, based on a preliminary action for an operation on a button or the like and a gesture input. For example, when a gesture based on the pressure distribution data matches a preset gesture or a learned gesture, the gesture input determination unit 17 can determine that the behavior of the occupant is a gesture for an operation input. Then, the gesture input determination unit 17 supplies gesture input information indicating that the gesture has been input to the device operation unit 21 and the seat control unit 22.

The body load determination unit 18 determines the physical load of the occupant seated on the seat 61 based on the statistically processed pressure distribution data supplied from the load change statistical processing unit 13. For example, the body load determination unit 18 can determine whether or not the occupant experiences accumulated physical fatigue due to being seated, based on the behavior of the occupant seated on the seat 61 and the time change of the behavior. Then, the body load determination unit 18 supplies body load information obtained according to the result of determination to the seat control unit 22. Further, the body load determination unit 18 can perform, based on the statistically processed pressure distribution data, seating determination processing of determining whether or not the occupant is seated on the seat 61 of the vehicle 51, and leaving determination processing for determining whether or not the occupant has left the seat 61 of the vehicle 51.

The mental and physical condition estimation unit 19 analyzes the physical information, heartbeat information, and respiratory information of the occupant seated on the seat 61, and estimates the mental and physical condition of the occupant seated on the seat 61. For example, the mental and physical condition estimation unit 19 can estimate the mental and physical condition such as a deviation of posture and a stress of the occupant, based on a difference between the behavior and/or biological activity of the occupant seated on the seat 61 and the daily deviation. Then, the mental and physical condition estimation unit 19 supplies mental and physical condition information obtained according to the result of estimation to the user notification unit 23 and the driving function notification unit 24.

The vehicle body motion measurement unit 20 is composed of a gyro sensor or the like capable of detecting triaxial acceleration, and measures the motion of the vehicle 51, such as acceleration, deceleration, or vibration. Then, the vehicle body motion measurement unit 20 supplies vehicle motion data obtained by measuring the motion of the vehicle 51 to the load change statistical processing unit 13, the body measurement unit 14, the heartbeat measurement unit 15, the respiration measurement unit 16, the gesture input determination unit 17, the body load determination unit 18, and the mental and physical condition estimation unit 19. For example, the vehicle motion measurement data is used to determine whether or not the behavior of the occupant is synchronized with the motion of the vehicle 51 in such a manner that the change in pressure distribution due to the sway of the vehicle 51 and the change in pressure distribution due to the behavior of the occupant in the processing performed by the respective units are separated. For example, when the vehicle body motion measurement unit 20 measures the vibration of the vehicle 51, the gesture input determination unit 17 can determine whether the behavior of the occupant is a gesture intended to be an operation input or a posture change not intended to be an operation input with the influence of the vibration of the vehicle 51 being eliminated.

The device operation unit 21 controls operations of various devices provided in the interior of the vehicle 51 equipped with the seat 61, for example, operations of entertainment devices and environmental control devices according to gesture input information supplied from the gesture input determination unit 17.

For example, the gesture input determination unit 17 detects the positions of both shoulders of the occupant based on the statistically processed pressure distribution data supplied from the load change statistical processing unit 13. Then, when the gesture input determination unit 17 outputs the gesture input information indicating that an operation of pushing the seat 61 with the right shoulder has been performed, the device operation unit 21 controls the volume of a corresponding entertainment device to turn up. On the other hand, when the gesture input determination unit 17 outputs the gesture input information indicating that an operation of pushing the seat 61 with the left shoulder has been performed, the device operation unit 21 controls the volume of the entertainment device to turn down. In this way, the device operation unit 21 can adjust the volume of the entertainment device.

The gesture input determination unit 17 also detects the centroid of the occupant based on the statistically processed pressure distribution data supplied from the load change statistical processing unit 13. Then, when the gesture input determination unit 17 outputs the gesture input information indicating that the action of moving the centroid up, down, left, or right has been performed, the device operation unit 21 controls the direction of the outlet of an air conditioner, which is a corresponding environmental control device, according to the up, down, left, or right movement of the centroid. In this way, the device operation unit 21 can adjust the wind direction of the air conditioner.

The seat control unit 22 controls various operation outputs to the movable parts of the seat 61 (the headrest part 62, the backrest part 63, the seat surface part 64, and the footrest part 65) according to the gesture input information supplied from the gesture input determination unit 17 and body load information supplied from the body load determination unit 18. For example, the seat control unit 22 controls the operation outputs so that the seat 61 is turned into forms, as described below with reference to FIGS. 3 and 4, corresponding to the gestures of the occupant according to the gesture input information.

Further, when the body load information indicates that the occupant experiences physical fatigue, the seat control unit 22 controls the operation outputs so that the seat 61 is turned into a form that relieves the physical fatigue of the occupant. For example, the seat control unit 22 detects reseating of the occupant based on the body load information, and evaluates the pressure distributions after the reseating in an integral manner for each corresponding part. If there is the resulting value for a part exceeds a set threshold value, the seat control unit 22 controls the seat 61 so as to relieve the pressure at that part. For example, the seat control unit 22 operates the backrest part 63 to adjust the reclining of the seat 61, thereby making it possible to relieve the accumulation of fatigue due to the occupant being seated.

The user notification unit 23 performs various user notifications such as, for example, notifying the user of a change in physical condition, and recommending taking a break to the user, according to the mental and physical condition information supplied from the mental and physical condition estimation unit 19.

The driving function notification unit 24 issues a notification about a predetermined driving function, such as changing the driving policy for automatic driving, according to the mental and physical condition information supplied from the mental and physical condition estimation unit 19.

In the control processing device 11 configured as described above, when the behavior of the occupant is determined to be a gesture for an operation input based on the pressure distribution data measured in the plurality of measurement ranges of the seat 61 on which the occupant is seated, the operation outputs for the seat 61 can be controlled according to the gesture. For example, the control processing device 11 can more accurately determine the gesture from the pressure distributions according to the behavior of the occupant and their time variations (e.g., the trajectory of the centroid), and therefore the control processing device 11 can reliably move the seat 61 so as to turn it into a form corresponding to the gesture. In this way, the control processing device 11 can reliably capture the gesture of the occupant and further improve the convenience.

Further, the control processing device 11 can reduce the stress and the like on the occupant by controlling the form of the seat 61 so that the seating state of the occupant is convenient and comfortable. Accordingly, for example, the level required by the occupant for sound quality, image quality, and the like is raised, and as a result, the worth of high-quality sound products, high-quality image products, and the like can be improved.

Furthermore, in the control processing device 11, the heartbeat measurement unit 15 measures the heartbeat from the propagation of a pressure change along the blood flow direction of the body, and calculates an LF/HF which is an index of autonomic nervous balance. As a result, the control processing device 11 can recline the seatback to encourage the occupant to relax for a lot of stress on the occupant, and can raise the seatback to encourage the occupant to awaken for a reduced degree of awakening of the occupant.

Further, in the control processing device 11, the respiration measurement unit 16 calculates the motion of the chest due to respiration from the time variations of the pressure distributions, and observes a reduced respiratory rate, a reduced ventilation volume, and expiratory-inspiratory balance and speed within a respiratory cycle. As a result, the control processing device 11 can measure the degree of awakening of the occupant, and when drowsiness is detected, the control processing device 11 moves a movable part of the seat 61, thereby making it possible to encourage the occupant to awaken and warn the occupant.

<Seat Control>

Figure 3:
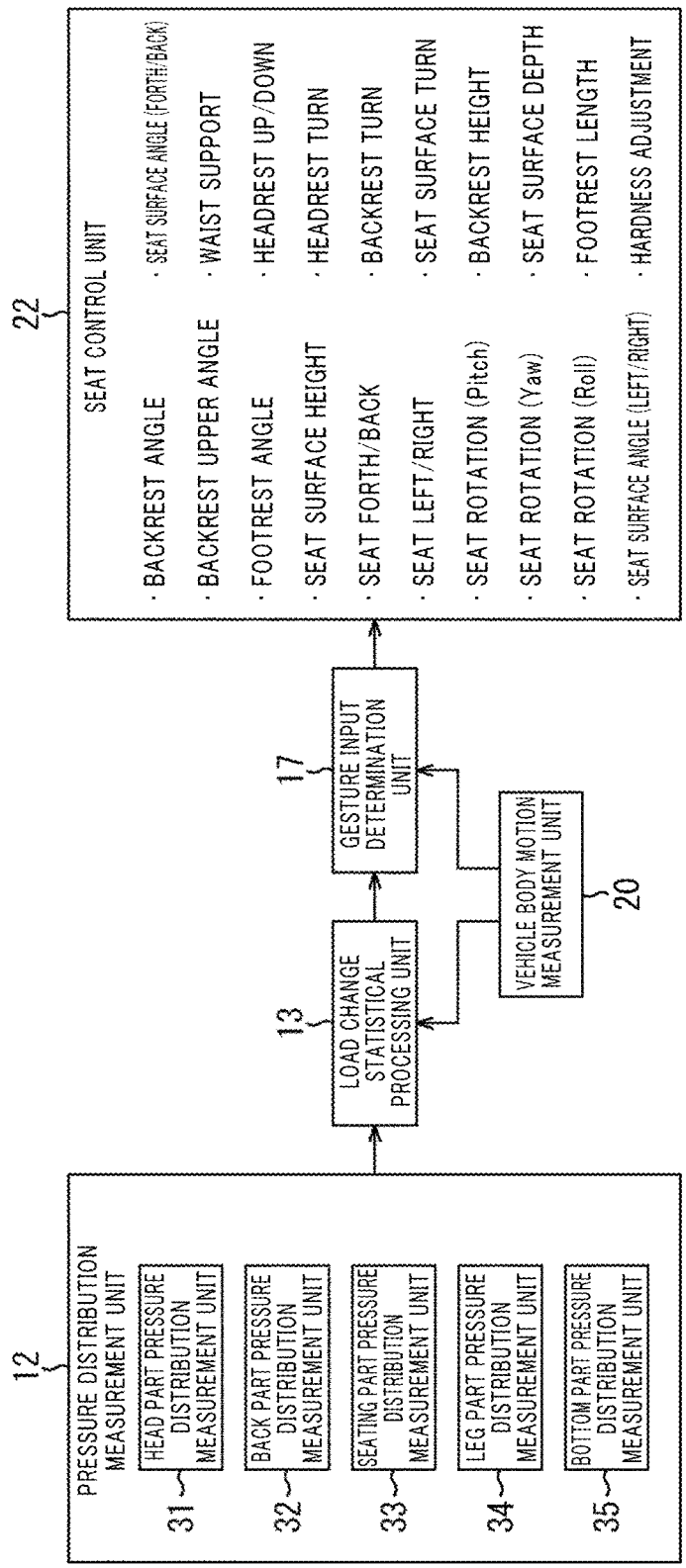
FIG. 3 is a diagram for explaining operation output control performed by a seat control unit.

Seat control performed by the seat control unit 22 will be described with reference to FIGS. 3 and 4. In FIG. 3, among the blocks constituting the control processing device 11, the blocks used for executing the seat control with a load change as an input are picked up and illustrated.

As illustrated in FIG. 3, in order to execute the seat control with a load change as an input, the pressure distribution measurement unit 12, the load change statistical processing unit 13, the gesture input determination unit 17, the vehicle body motion measurement unit 20, and the seat control unit 22 are used. Then, as an operation output for the seat control unit 22 to control the seat 61, for example, backrest angle, backrest upper angle, footrest angle, seat surface height, seat forth/back, seat left/right, seat rotation (Pitch), seat rotation (Yaw), seat rotation (Roll), seat surface angle (right/left), seat surface angle (forth/back), waist support, headrest up/down, headrest turn, backrest turn, seat surface turn, backrest height, seat surface depth, footrest length, and hardness adjustment.

Figure 4:
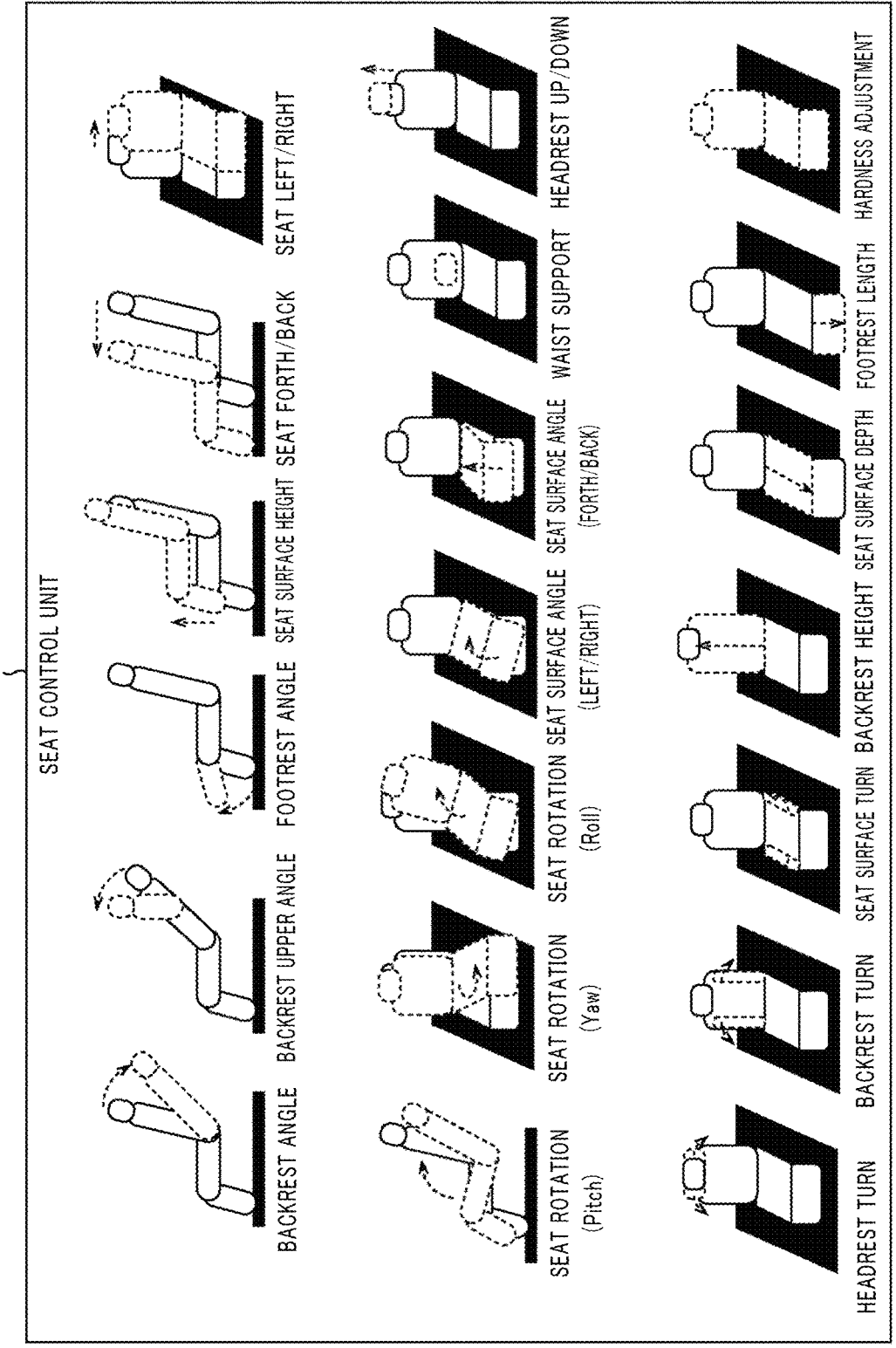
FIG. 4 is a diagram for explaining operation output control performed by the seat control unit.

Specifically, as illustrated in FIG. 4, with the backrest angle, the operation output is controlled so as to adjust the angle of the backrest part 63. With the backrest upper angle, the operation output is controlled so as to adjust the angle of the upper half of the backrest part 63. With the footrest angle, the operation output is controlled so as to adjust the angle of the footrest part 65. With the seat height, the operation output is controlled so as to adjust the height of the entire seat 61. With the seat forth/back, the operation output is controlled so as to adjust the position of the entire seat 61 in the front-rear direction. With the seat left/right, the operation output is controlled so as to adjust the position of the entire seat 61 in the left-right direction.

With the seat rotation (Pitch), the operation output is controlled so as to adjust the rotation angle of the entire seat 61 in the pitch direction. With the seat rotation (Yaw), the operation output is controlled so as to adjust the rotation angle of the entire seat 61 in the yaw direction. With the seat rotation (Roll), the operation output is controlled so as to adjust the rotation angle of the entire seat 61 in the roll direction. With the seat surface angle (left/right), the operation output is controlled so as to adjust the rotations of the seat surface part 64 and the footrest part 65 in the left-right direction. With the seat surface angle (forth/back), the operation output is controlled so as to adjust the rotations of the seat surface part 64 and the footrest part 65 in the front-rear direction.

With the waist support, the operation output is controlled so as to adjust the amount of protrusion of a waist support portion arranged to protrude from a waist portion of the backrest part 63. With the headrest up/down, the operation output is controlled so as to adjust the height of the headrest part 62 in the up-down direction. With the headrest turn, the operation output is controlled so as to adjust the amount of turn of left and right wings of the headrest part 62. With the backrest turn, the operation output is controlled so as to adjust the amount of turn of left and right wings of the backrest part 63. With the seat surface turn, the operation output is controlled so as to adjust the amount of turn of left and right wings of the seat surface part 64.

With the backrest height, the operation output is controlled so as to adjust the height of the backrest part 63. With the seat surface depth, the operation output is controlled so as to adjust the depth of the seat surface part 64. With the footrest length, the operation output is controlled so as to adjust the length of the footrest part 65. With the hardness adjustment, the operation output is controlled so as to adjust the hardness or softness of cushions of the headrest part 62, the backrest part 63, the seat surface part 64, and the footrest part 65.

In this way, in the control processing device 11, the operation outputs of the seat control unit 22 with respect to the movable parts of the seat 61 are controlled, and, for example, the seat 61 is deformed so as to have a shape corresponding to the gesture of the occupant determined by the gesture input determination unit 17 based on the pressure distribution data.

<Seat Control>

Statistical processing in the load change statistical processing unit 13 will be described with reference to FIGS. 5 to 13.

Figure 5:
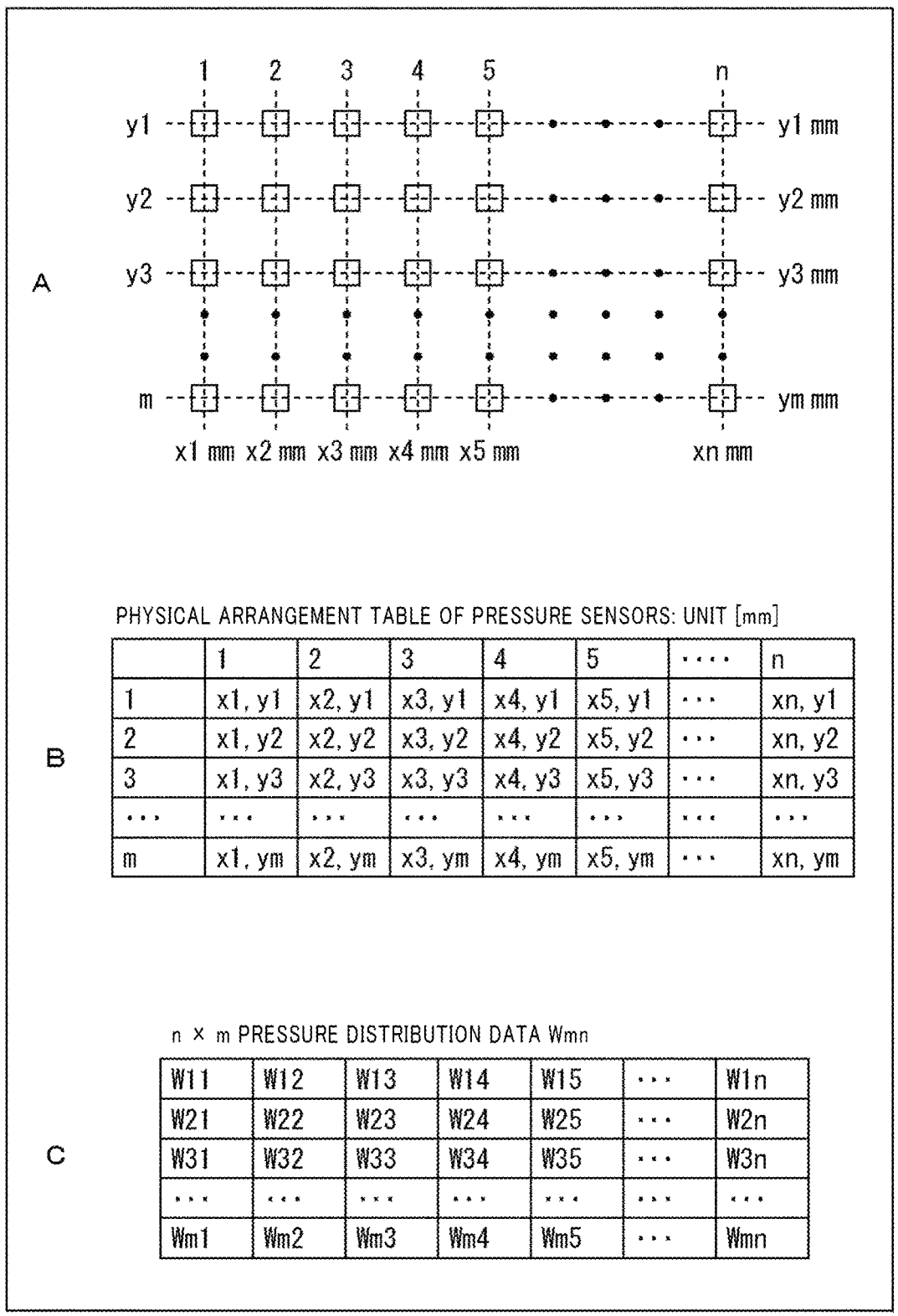
FIG. 5 illustrates an arrangement of a pressure sensor and examples of pressure distribution data.

For example, as illustrated in A of FIG. 5, n×m pressure sensors are arranged in x and y directions in each measurement range illustrated in FIG. 2. Note that although A of FIG. 5 illustrates a logical arrangement in which n×m pressure sensors are arranged at equal pitches, it is not necessary that they are arranged at equal pitches.

In a physical arrangement table illustrated in B of FIG. 5, the X coordinate and the Y coordinate (in millimeter) of each pressure sensor are registered as a physical arrangement of n×m pressure sensors. Then, based on pressure data output from the n×m pressure sensors, pressure distribution data Wmn as illustrated in C of FIG. 5 is acquired.

Using such pressure distribution data Wmn, the load change statistical processing unit 13 can obtain a load sum Wsum according to the following Equation (1).

[Math. 1]

$$Wsum = \sum_{i=1}^{n} \sum_{j=1}^{m} Wij \quad (1)$$

Further, the load change statistical processing unit 13 can obtain a barycenter x-coordinate Cx and a barycenter y-coordinate Cy according to the following Equation (2) using the pressure distribution data Wmn and the load sum Wsum.

[Math. 2]

$$\begin{cases} Cx = \dfrac{\sum_{i=1}^{n} xi\left(\sum_{j=1}^{m} Wij\right)}{Wsum} \\ Cy = \dfrac{\sum_{j=1}^{m} yj\left(\sum_{i=1}^{n} Wij\right)}{Wsum} \end{cases} \quad (2)$$

Further, when load measurement values of a table as illustrated in A of FIG. 6 are obtained, the load change statistical processing unit 13 classifies the load measurement values according to a threshold value, so that a load distribution shape as illustrated in B of FIG. 6 can be obtained. An example of the load distribution shape is illustrated in B of FIG. 6 in which "1" is set for the coordinates of the pressure sensor that detects a load measurement value of equal to or larger than a threshold value of 5, and "0" is set for the coordinates of the pressure sensor that detects a load measurement value of smaller than the threshold value of 5.

Then, the load change statistical processing unit 13 multiplies the load distribution shape by physical areas Anm of places where the respective pressure sensors are arranged, so that a load area distribution as illustrated in C of FIG. 6 can be obtained.

For example, the physical area Anm for each of the places where the pressure sensors are arranged is obtained by the following Equation (3) using the X coordinate x(n+1) of an adjacent pressure sensor on the positive side in the X direction, the X coordinate x(n−1) of an adjacent pressure sensor on the negative side in the X direction, the Y coordinate y(m+1) of an adjacent pressure sensor on the positive side in the Y direction, and the Y coordinate y(m−1) of an adjacent pressure sensor on the negative side in the Y direction.

[Math. 3]

$$Anm = \frac{(x(n-1) + x(n+1))(y(m-1) + y(m+1))}{4} \quad (3)$$

Accordingly, a physical area table of the pressure sensors as illustrated in FIG. 7 is acquired by using the X and Y coordinates of the pressure sensors registered in the physical arrangement table illustrated in B of FIG. 5.

The load change statistical processing unit 13 can also obtain a load area Mum, a moving average value of the load area SAve_Asum(t), and a moving variance value of the load area SS2_Asum(t), by the following Equation (4).

[Math. 4]

$$\begin{cases} Asum = \sum_{i=1}^{n} \sum_{j=1}^{m} Aij \\ SAve\_Asum(t) = \dfrac{1}{S+1} \sum_{i=t}^{t-S} Asum(i) \\ SS2\_Asum(t) = \dfrac{1}{S+1} \sum_{i=t}^{t-S} (Asum(i) - SAve\_Asum(t))^2 \end{cases} \quad (4)$$

Figure 8:
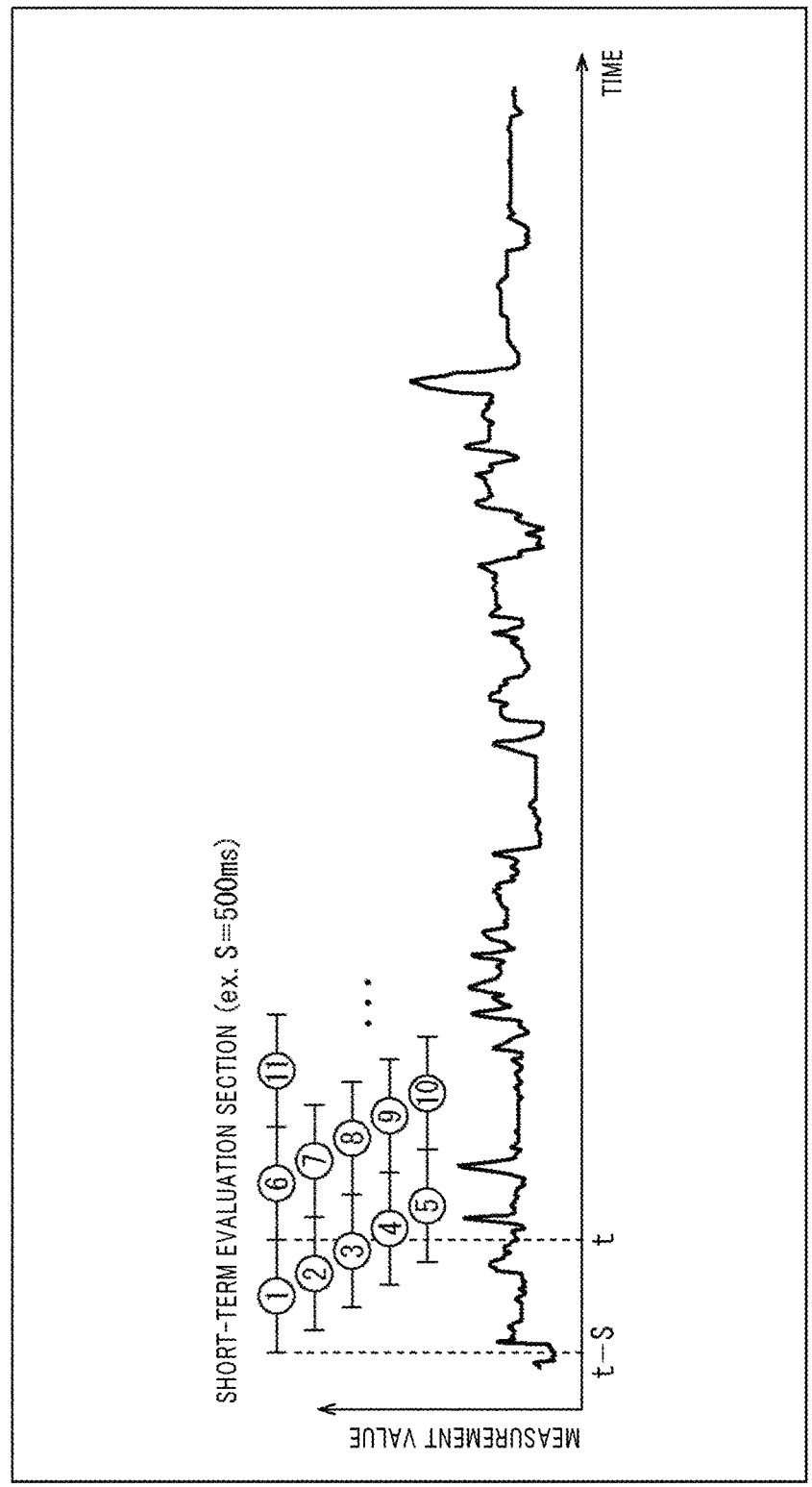
FIG. 8 illustrates an example of a short-term evaluation section.

Here, in Equation (4), a short-term section S is used as a short-term section for which statistical average and variance values are to be obtained. For example, the short-term section S is set to 500 ms as illustrated in FIG. 8. In the example illustrated in FIG. 8, the short-term section S is set to slide in a shorter section (e.g., 100 ms), and an average value and a variance value are obtained for each short-term section S.

Figure 9:
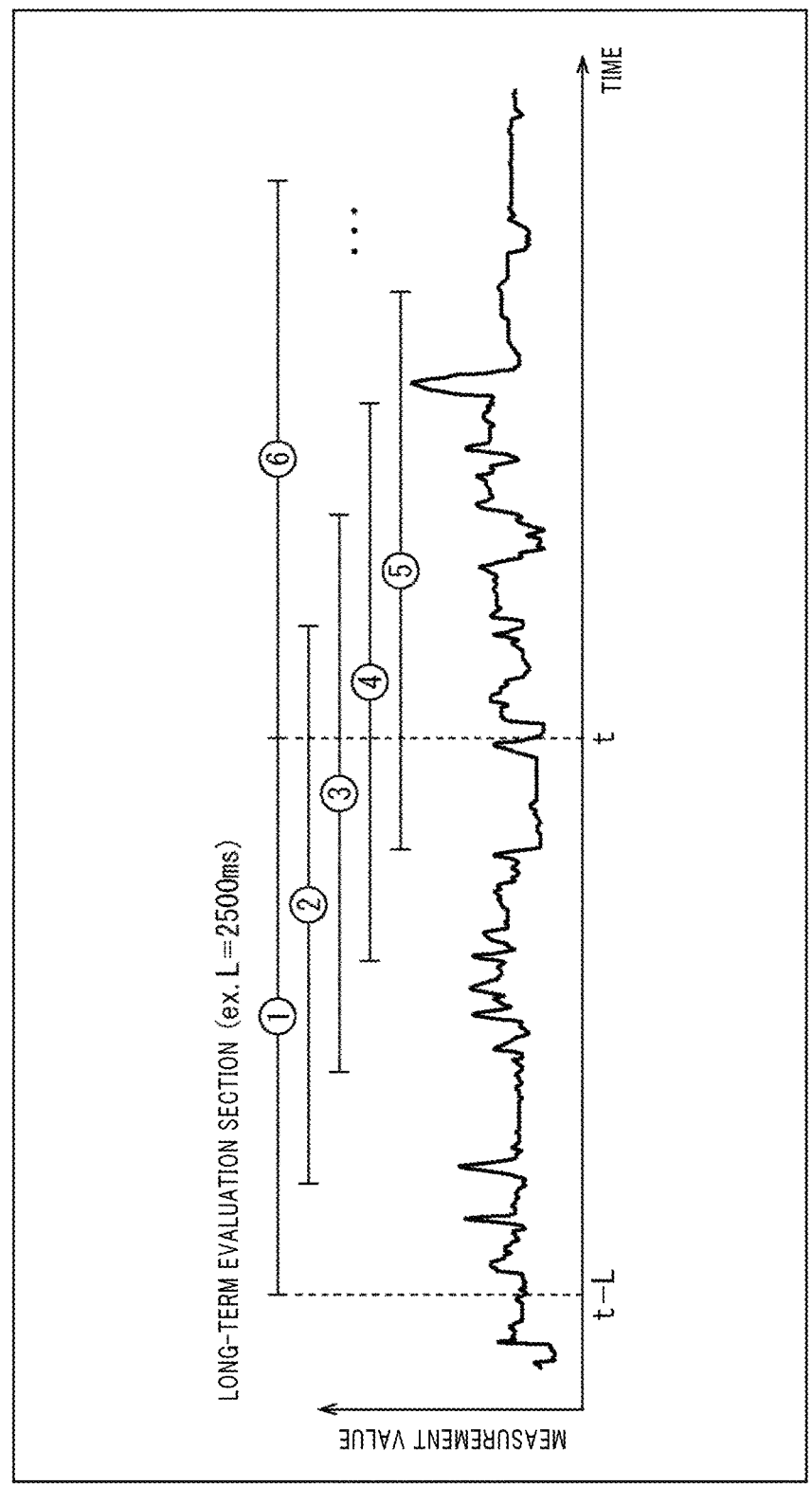
FIG. 9 illustrates an example of a long-term evaluation section.

Further, as will be described below, a long-term section L is used as a long-term section for which statistical average and variance values are to be obtained. For example, the long-term section L is set to 2500 ms as illustrated in FIG. 9. In the example illustrated in FIG. 9, the long-term section L is set to slide in a shorter section (e.g., 500 ms of the short-term section S), and an average value and a variance value are obtained for each long-term section L.

Accordingly, as illustrated in FIG. 10, the load change statistical processing unit 13 can calculate a load sum short-term section average value SAve_Wsum(t), centroid coordinate short-term section average values [SAve_Cx(t), SAve_Cy(t)], a load sum short-term section variance value SS2_Wsum(t), and centroid coordinate short-term section variance values [SS2_Cx(t), SS2_Cy(t)].

Similarly, as illustrated in FIG. 11, the load change statistical processing unit 13 can calculate a load sum long-term section average value LAve_Wsum(t), centroid coordinate long-term section average values [LAve_Cx(t), LAve_Cy(t)], a load sum long-term section variance value LS2_Wsum(t), and centroid coordinate long-term section variance values [LS2_Cx(t), LS2_Cy(t)].

Further, the load change statistical processing unit 13 can obtain a load distribution shape as illustrated in B of FIG. 6 described above, and evaluate the change in the load distribution shape in each of the short-term section S and the long-term section L.

Figure 12:
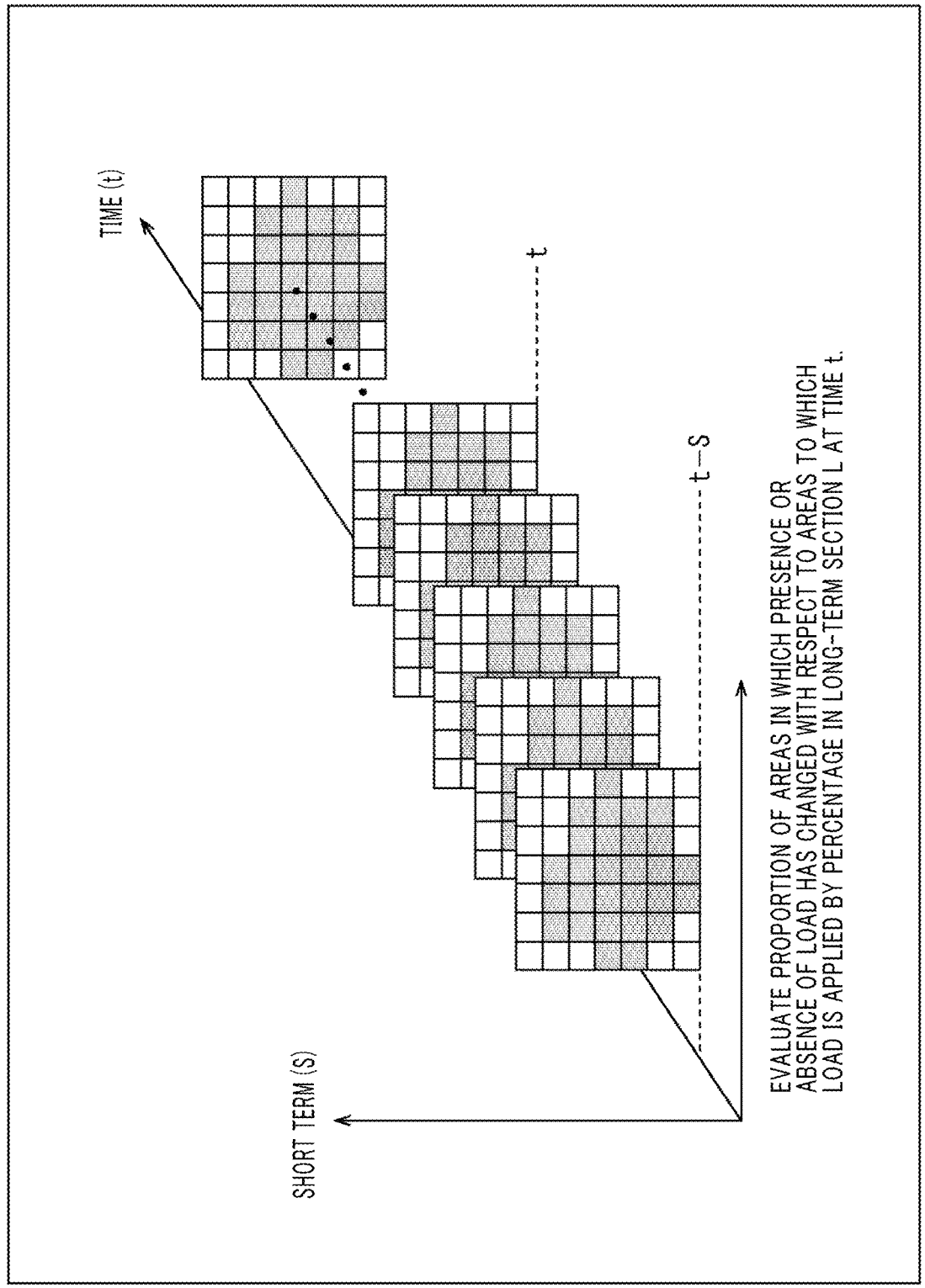
FIG. 12 illustrates an example of changes in a load distribution shape in short-term sections.

For example, as illustrated in FIG. 12, the load change statistical processing unit 13 can arrange load distribution shapes along the time direction, and evaluate the proportion of areas in which the presence or absence of load has changed with respect to areas to which load is applied by percentage in the short-term section S at each time t.

Figure 13:
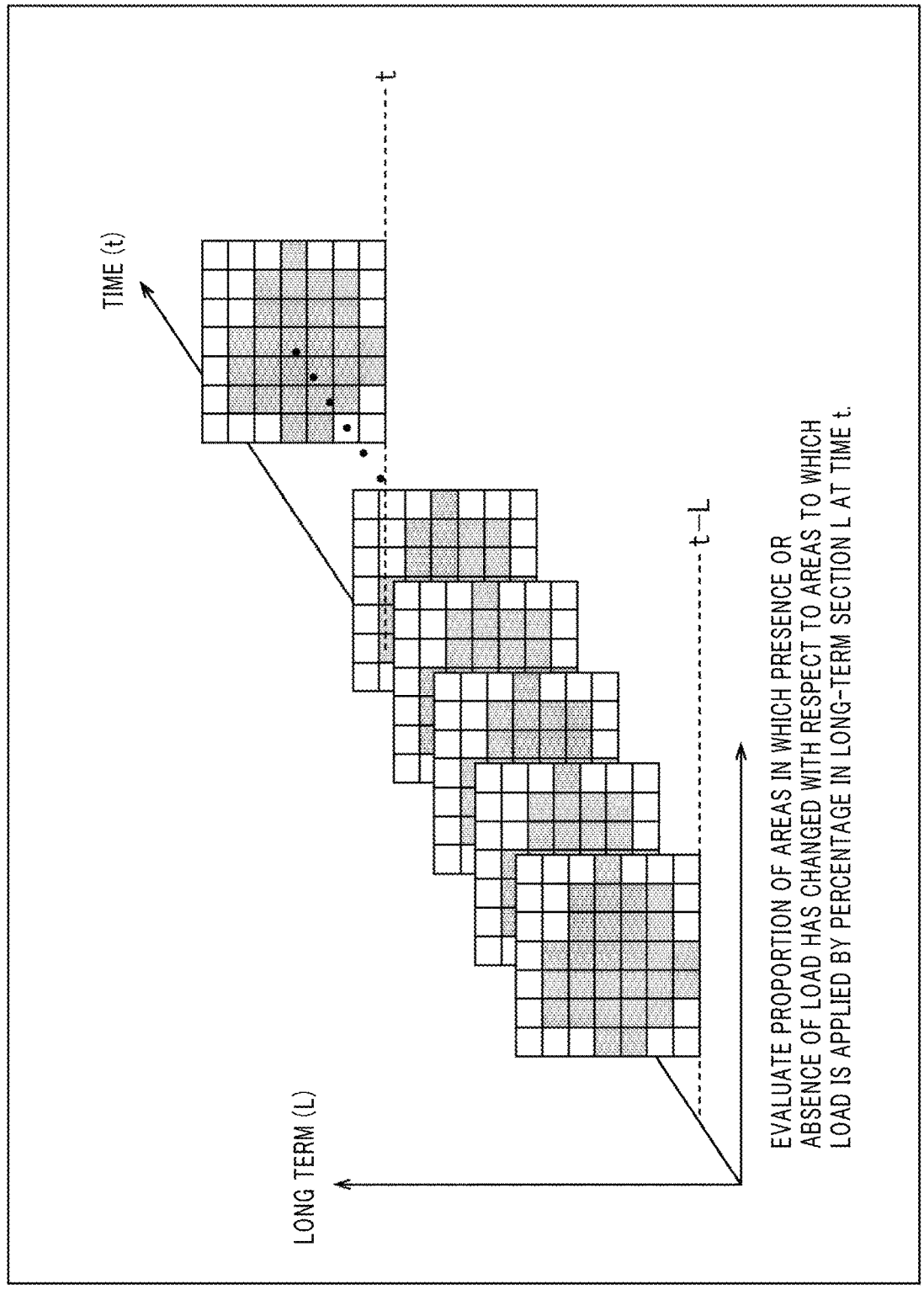
FIG. 13 illustrates an example of changes in a load distribution shape in long-term sections.

Similarly, as illustrated in FIG. 13, the load change statistical processing unit 13 can arrange load distribution shapes along the time direction, and evaluate the proportion of areas in which the presence or absence of load has changed with respect to areas to which load is applied by percentage in the long-term section L at each time t.

<Pressure Distribution Measurement Processing and Load Change Statistical Processing>

With reference to a flowchart illustrated in FIG. 14, pressure distribution measurement processing performed by the pressure distribution measurement unit 12 (steps S11 to S13) and load change statistical processing performed by the load change statistical processing unit 13 (steps S14 to S25) will be described.

In step S11, the pressure distribution measurement unit 12 acquires pressure distribution data in each part of the seat 61 from the head part pressure distribution measurement unit 31, the back part pressure distribution measurement unit 32, the seating part pressure distribution measurement unit 33, the leg part pressure distribution measurement unit 34, and the bottom part pressure distribution measurement unit 35.

In step S12, the pressure distribution measurement unit 12 sets a vibration element included in the vehicle motion data measured by the vehicle body motion measurement unit 20 as vibration reference data, and removes vibration noise from the pressure distribution data acquired in step S11 with reference to the vibration reference data.

In step S13, the pressure distribution measurement unit 12 periodically acquires, for example, an average value of pressure data output from the pressure sensor in the leaving state, and uses the average value as calibration data to perform data correction (zero-point correction) on the pressure distribution data from which the vibration noise has been removed in step S12.

Then, after the pressure distribution measurement unit 12 supplies the pressure distribution data subjected to the data correction in step S13 to the load change statistical processing unit 13, processing of steps S14 to S17 is performed in parallel.

In step S14, the load change statistical processing unit 13 calculates a centroid x-coordinate Cx and a centroid y-coordinate Cy based on the pressure distribution data supplied from the pressure distribution measurement unit 12 by the above-described Equation (2).

In step S15, the load change statistical processing unit 13 calculates a load sum Wsum based on the pressure distribution data supplied from the pressure distribution measurement unit 12 by the above-described Equation (1).

In step S16, the load change statistical processing unit 13 calculates a load area Asum based on the pressure distribution data supplied from the pressure distribution measurement unit 12 by the above-described Equation (3) and Equation (4).

In step S17, the load change statistical processing unit 13 calculates a load distribution shape based on the pressure distribution data supplied from the pressure distribution measurement unit 12, as described above with reference to FIG. 6.

Here, the processing of steps S14 to S17 is performed every time the pressure distribution data is supplied from the pressure distribution measurement unit 12 to the load change statistical processing unit 13. Then, when the processing results of the processing of steps S14 to S17 for the pressure distribution data in the short-term section S as illustrated in FIG. 8 are accumulated, processing of steps S18 to S21 is sequentially performed in parallel.

In step S18, the load change statistical processing unit 13 calculates an average value and a variance value in the short-term section S for the centroid x-coordinate Cx and the centroid y-coordinate Cy calculated in step S14 for each measurement part of the seat 61.

In step S19, the load change statistical processing unit 13 calculates an average value and a variance value in the short-term section S for the total load Wsum calculated in step S15 for each measurement part of the seat 61.

In step S20, the load change statistical processing unit 13 calculates an average value and a variance value in the short-term section S for the load area Asum calculated in step S16 for each measurement part of the seat 61.

In step S21, the load change statistical processing unit 13 calculates a change in the short-term section S for the load distribution shape calculated in step S17, as described above with reference to FIG. 12.

Further, in parallel with the processing of steps S18 to S20, when the processing results of the processing of steps S14 to S17 for the pressure distribution data of the long-term section L as illustrated in FIG. 9 are accumulated, processing of steps S22 to S25 is sequentially performed in parallel.

In step S22, the load change statistical processing unit 13 calculates an average value and a variance value in the long-term section L for the centroid x-coordinate Cx and the centroid y-coordinate Cy calculated in step S14 for each measurement part of the seat 61.

In step S23, the load change statistical processing unit 13 calculates an average value and a variance value in the long-term section L for the load sum Wsum calculated in step S15 for each measurement part of the seat 61.

In step S24, the load change statistical processing unit 13 calculates an average value and a variance value in the long-term section L for the load area Asum calculated in step S16 for each measurement part of the seat 61.

In step S25, the load change statistical processing unit 13 calculates a change in the long-term section L for the load distribution shape calculated in step S17, as described above with reference to FIG. 13.

Then, when the processing of steps S22 to S25 ends, the pressure distribution measurement processing and the load change statistical processing also end.

Here, in each of the above steps, the load change statistical processing unit 13 calculates an average value and a variance value for each of the measurement parts of the seat 61, that is, the headrest part 62, the backrest part 63, the seat surface part 64, and the footrest part 65 illustrated in FIG. 2.

For example, in step S18, the load change statistical processing unit 13 obtains, for the average value in the short-term section S for the centroid x-coordinate, a headrest centroid x-coordinate short-term section average value SAve_Cx_HR, a backrest centroid x-coordinate short-term section average value SAve_Cx_BR, a seat centroid x-coordinate short-term section average value SAve_Cx_SE, a footrest right centroid x-coordinate short-term section average value SAve_Cx_FR-R, a footrest left centroid x-coordinate short-term section average value SAve_Cx_FR-L, a floor right centroid x-coordinate short-term section average value SAve_Cx_FL-R, and a floor left centroid x-coordinate short-term section average value SAve_Cx_FL-L.

In step S18, the load change statistical processing unit 13 also obtains, for the variance value in the short-term section S for the centroid x-coordinate, a headrest centroid x-coordinate short-term section variance value SS2_Cx_HR, a backrest centroid x-coordinate short-term section variance value SS2_Cx_BR, a seat centroid x-coordinate short-term section variance value SS2_Cx_SE, a footrest right centroid x-coordinate short-term section variance value SS2_Cx_FR-R, a footrest left centroid x-coordinate short-term section variance value SS2_Cx_FR-L, a floor right centroid x-coordinate short-term section variance value SS2_Cx_FL-R, and a floor left centroid x-coordinate short-term section variance value SS2_Cx_FL-L.

Similarly, in step S18, the load change statistical processing unit 13 obtains, for the average value in the short-term section S for the centroid y-coordinate, a headrest centroid y-coordinate short-term section average value SAve_Cy_HR, a backrest centroid y-coordinate short-term section average value SAve_Cy_BR, a seat centroid y-coordinate short-term section average value SAve_Cy_SE, a footrest right centroid y-coordinate short-term section average value SAve_Cy_FR-R, a footrest left centroid y-coordinate short-term section average value SAve_Cy_FR-L, a floor right centroid y-coordinate short-term section average value SAve_Cy_FL-R, and a floor left centroid y-coordinate short-term section average value SAve_Cy_FL-L.

Further, in step S18, the load change statistical processing unit 13 also obtains, for the variance value in the short-term section S for the centroid y-coordinate, a headrest centroid y-coordinate short-term section variance value SS2_Cy_HR, a backrest centroid y-coordinate short-term section variance value SS2_Cy_BR, a seat centroid y-coordinate short-term section variance value SS2_Cy_SE, a footrest right centroid y-coordinate short-term section variance value SS2_Cy_FR-R, a footrest left centroid y-coordinate short-term section variance value SS2_Cy_FR-L, a floor right centroid y-coordinate short-term section variance value SS2_Cy_FL-R, and a floor left centroid y-coordinate short-term section variance value SS2_Cy_FL-L.

Then, in step S19, the load change statistical processing unit 13 obtains, for the average value in the short-term section S for the load sum, a headrest load sum short-term section average value SAve_Wsum_HR, a backrest load sum short-term section average value SAve_Wsum_BR, a seat load sum short-term section average value SAve_Wsum_SE, a footrest right load sum short-term section average value SAve_Wsum_FR-R, a footrest left load sum short-term section average value SAve_Wsum_FR-L, a floor right load sum short-term section average value SAve_Wsum_FL-R, and a floor left load sum short-term section average value SAve_Wsum_FL-L.

Similarly, in step S19, the load change statistical processing unit 13 obtains, for the variance value in the short-term section S for the load sum, a headrest load sum short-term section variance value SS2_Wsum_HR, a backrest load sum short-term section variance value SS2_Wsum_BR, a seat load sum short-term section variance value SS2_Wsum_SE, a footrest right load sum short-term section variance value SS2_Wsum_FR-R, a footrest left load sum short-term section variance value SS2_Wsum_FR-L, a floor right load sum short-term section variance value SS2_Wsum_FL-R, and a floor left load sum short-term section variance value SS2_Wsum_FL-L.

Further, in step S22, the load change statistical processing unit 13 obtains, for the average value in the long-term section L for the centroid x-coordinate, a headrest centroid x-coordinate long-term section average value LAve_Cx_HR, a backrest centroid x-coordinate long-term section average value LAve_Cx_BR, a seat centroid x-coordinate long-term section average value LAve_Cx_SE, a footrest right centroid x-coordinate long-term section average value LAve_Cx_FR-R, a footrest left centroid x-coordinate long-term section average value LAve_Cx_FR-L, a floor right centroid x-coordinate long-term section average value LAve_Cx_FL-R, and a floor left centroid x-coordinate long-term section average value LAve_Cx_FL-L.

In step S22, the load change statistical processing unit 13 also obtains, for the variance value in the long-term section L for the centroid x-coordinate, a headrest centroid x-coordinate long-term section variance value LS2_Cx_HR, a backrest centroid x-coordinate long-term section variance value LS2_Cx_BR, a seat centroid x-coordinate long-term section variance value LS2_Cx_SE, a footrest right centroid x-coordinate long-term section variance value LS2_Cx_FR-R, a footrest left centroid x-coordinate long-term section variance value LS2_Cx_FR-L, a floor right centroid x-coordinate long-term section variance value LS2_Cx_FL-R, and a floor left centroid x-coordinate long-term section variance value LS2_Cx_FL-L.

Similarly, in step S22, the load change statistical processing unit 13 obtains, for the average value in the long-term section L for the centroid y-coordinate, a headrest centroid y-coordinate long-term section average value LAve_Cy_HR, a backrest centroid y-coordinate long-term section average value LAve_Cy_BR, a seat centroid y-coordinate long-term section average value LAve_Cy_SE, a footrest right centroid y-coordinate long-term section average value LAve_Cy_FR-R, a footrest left centroid y-coordinate long-term section average value LAve_Cy_FR-L, a floor right centroid y-coordinate long-term section average value LAve_Cy_FL-R, and a floor left centroid y-coordinate long-term section average value LAve_Cy_FL-L.

In step S22, the load change statistical processing unit 13 also obtains, for the variance value in the long-term section L for the centroid y-coordinate, a headrest centroid y-coordinate long-term section variance value LS2_Cy_HR, a backrest centroid y-coordinate long-term section variance value LS2_Cy_BR, a seat centroid y-coordinate long-term section variance value LS2_Cy_SE, a footrest right centroid y-coordinate long-term section variance value LS2_Cy_FR-R, a footrest left centroid y-coordinate long-term section variance value LS2_Cy_FR-L, a floor right centroid y-coordinate long-term section variance value LS2_Cy_FL-R, and a floor left centroid y-coordinate long-term section variance value LS2_Cy_FL-L.

Then, in step S23, the load change statistical processing unit 13 obtains, for the average value in the long-term section L for the load sum, a headrest load sum long-term section average value LAve_Wsum_HR, a backrest load sum long-term section average value LAve_Wsum_BR, a seat load sum long-term section average value LAve_Wsum_SE, a footrest right load sum long-term section average value LAve_Wsum_FR-R, a footrest left load sum long-term section average value LAve_Wsum_FR-L, a floor right load sum long-term section average value LAve_Wsum_FL-R, and a floor left load sum long-term section average value LAve_Wsum_FL-L.

Similarly, in step S23, the load change statistical processing unit 13 obtains, for the variance value in the long-term section L for the load sum, a headrest load sum long-term section variance value LS2_Wsum_HR, a backrest load sum long-term section variance value LS2_Wsum_BR, a seat load sum long-term section variance value LS2_Wsum_SE, a footrest right load sum long-term section variance value LS2_Wsum_FR-R, a footrest left load sum long-term section variance value LS2_Wsum_FR-L, a floor right load sum long-term section variance value LS2_Wsum_FL-R, and a floor left load sum long-term section variance value LS2_Wsum_FL-L.

<Vehicle Body Motion Measurement Processing>

The vehicle body motion measurement processing performed by the vehicle body motion measurement unit 20 will be described with reference to a flowchart illustrated in FIG. 15.

In step S31, the vehicle body motion measurement unit 20 acquires acceleration data from, for example, a gyro sensor (not illustrated).

In step S32, the vehicle body motion measurement unit 20 periodically acquires an average value of acceleration data output from the gyro sensor in the leaving state, and uses the average value as calibration data to perform data correction (zero-point correction) on the acceleration data acquired in step S31.

In step S33, the vehicle body motion measurement unit 20 performs frequency separation on the acceleration data subjected to the data correction in step S32, in which the acceleration data is separated into a low frequency band (e.g., 1 Hz or less), a medium frequency band (e.g., 1 to 10 Hz), and a high frequency band (e.g., 10 Hz or more).

After that, processing of steps S34 to S36 is performed in parallel.

In step S34, the vehicle body motion measurement unit 20 calculates a low-band vehicle body displacement amount Body_LF of the vehicle 51 by using the acceleration data in the low frequency band.

In step S35, the vehicle body motion measurement unit 20 calculates a medium-band vehicle body displacement amount Body_MF of the vehicle 51 by using the acceleration data in the medium frequency band.

In step S36, the vehicle body motion measurement unit 20 calculates a high-band vehicle body displacement amount Body_HF of the vehicle 51 by using the acceleration data in the high frequency band.

Then, when the processing of steps S34 to S36 ends, the vehicle body motion measurement processing also ends.

For example, the low-band vehicle body displacement amount Body_LF of the vehicle 51 that exhibits an acceleration sufficiently lower than a displacement speed generated by the behavior of a person is acquired based on the acceleration data in the low frequency band. Since such an acceleration data in the low frequency band affects the load measurement, the determination using the load measurement is stopped when the low-band vehicle body displacement amount Body_LF is large. Further, controlling the operation outputs based on the low-band vehicle body displacement amount Body_LF so as to perform headrest turning and backrest turning as illustrated in FIG. 4 makes it possible to hold the occupant's body.

Further, the medium-band vehicle body displacement amount Body_MF of the vehicle 51 that exhibits almost the same acceleration as a displacement speed generated by the behavior of a person is acquired based on the acceleration data in the medium frequency band. Since such an acceleration data in the medium frequency band affects the load measurement, the determination using the load measurement is stopped when the medium-band vehicle body displacement amount Body_MF is large.

Further, the high-band vehicle body displacement amount Body_HF of the vehicle 51 that exhibits an acceleration sufficiently higher than a displacement speed generated by the behavior of a person is acquired based on the acceleration data in the high frequency band. Such acceleration data in the high frequency band typically has a small displacement, and is unlikely to affect the load measurement. Note that if the high-band vehicle body displacement amount Body_HF is excessive, the determination using the load measurement is stopped.

<Seat Control>

Figure 16:
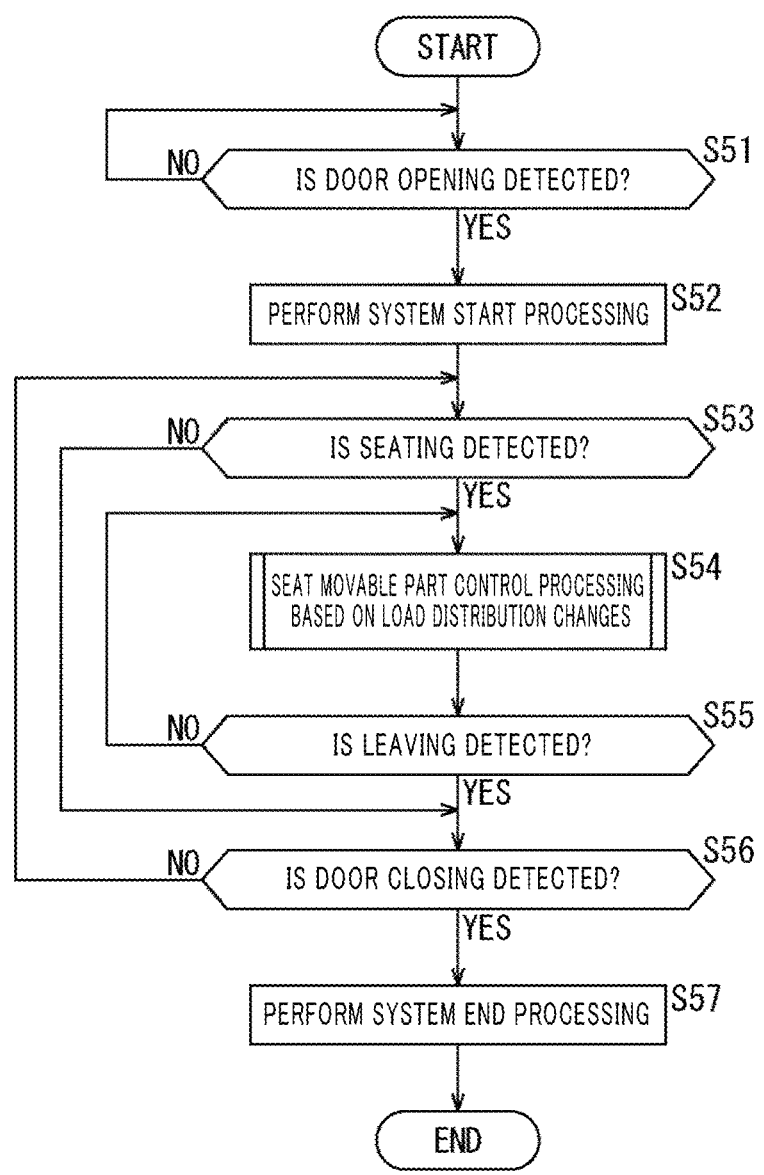
FIG. 16 is a flowchart illustrating control processing performed by the control processing device.

A flowchart of FIG. 16 is a flowchart for explaining the overall control processing performed by the control processing device 11.

In step S51, the control processing device 11 determines whether or not a door of the vehicle 51 opening is detected.

In step S51, the processing is on standby until the control processing device 11 determines that a door of the vehicle 51 opening is detected. When it is determined that a door of the vehicle 51 opening is detected, the processing proceeds to step S52.

In step S52, the control processing device 11 performs processing necessary to start the system. For example, the control processing device 11 starts the pressure distribution measurement processing and the load change statistical processing described with reference to FIG. 14 described above, and starts the vehicle body motion measurement processing described with reference to FIG. 15 described above.

In step S53, the control processing device 11 determines whether or not the occupant being seated on the seat 61 of the vehicle 51 is detected.

In step S53, when the control processing device 11 determines that the seating is detected, the processing proceeds to step S54, and then seat movable part control processing (described below with reference to FIGS. 17 and 18) based on load distribution changes is performed.

When the seat movable part control processing based on the load distribution changes performed in step S54 ends, the control processing device 11 determines whether or not the occupant leaving the seat 61 of the vehicle 51 is detected in step S55.

In step S55, when the control processing device 11 determines that the occupant leaving the seat 61 of the vehicle 51 is not detected, the processing returns to step S54, and then the seat movable part control processing based on the load distribution changes is continued.

On the other hand, when it is determined in step S53 that the control processing device 11 determines that the seating is not detected, or when it is determined in step S55 that the control processing device 11 determines that the leaving is detected, the processing proceeds to step S56.

In step S56, the control processing device 11 determines whether or not the door of the vehicle 51 closing is detected.

When the control processing device 11 determines in step S56 that the door of the vehicle 51 closing is not detected, the processing returns to step S53, and then the same processing is repeated thereafter.

On the other hand, when it is determined in step S56 that the control processing device 11 determines that the door of the vehicle 51 closing is detected, the processing proceeds to step S57. In other words, this means that the door is closed with no occupant being in the vehicle 51.

In step S57, the control processing device 11 performs processing necessary to end the system (e.g., end the pressure distribution measurement processing, the load change statistical processing, and the vehicle body motion measurement processing which have been started in step S52), and then the processing ends.

<Seat Movable Part Control Processing Based on Load Distribution Changes>

A state transition in the seat movable part control processing based on load distribution changes will be described with reference to FIGS. 17 and 18.

Figure 17:
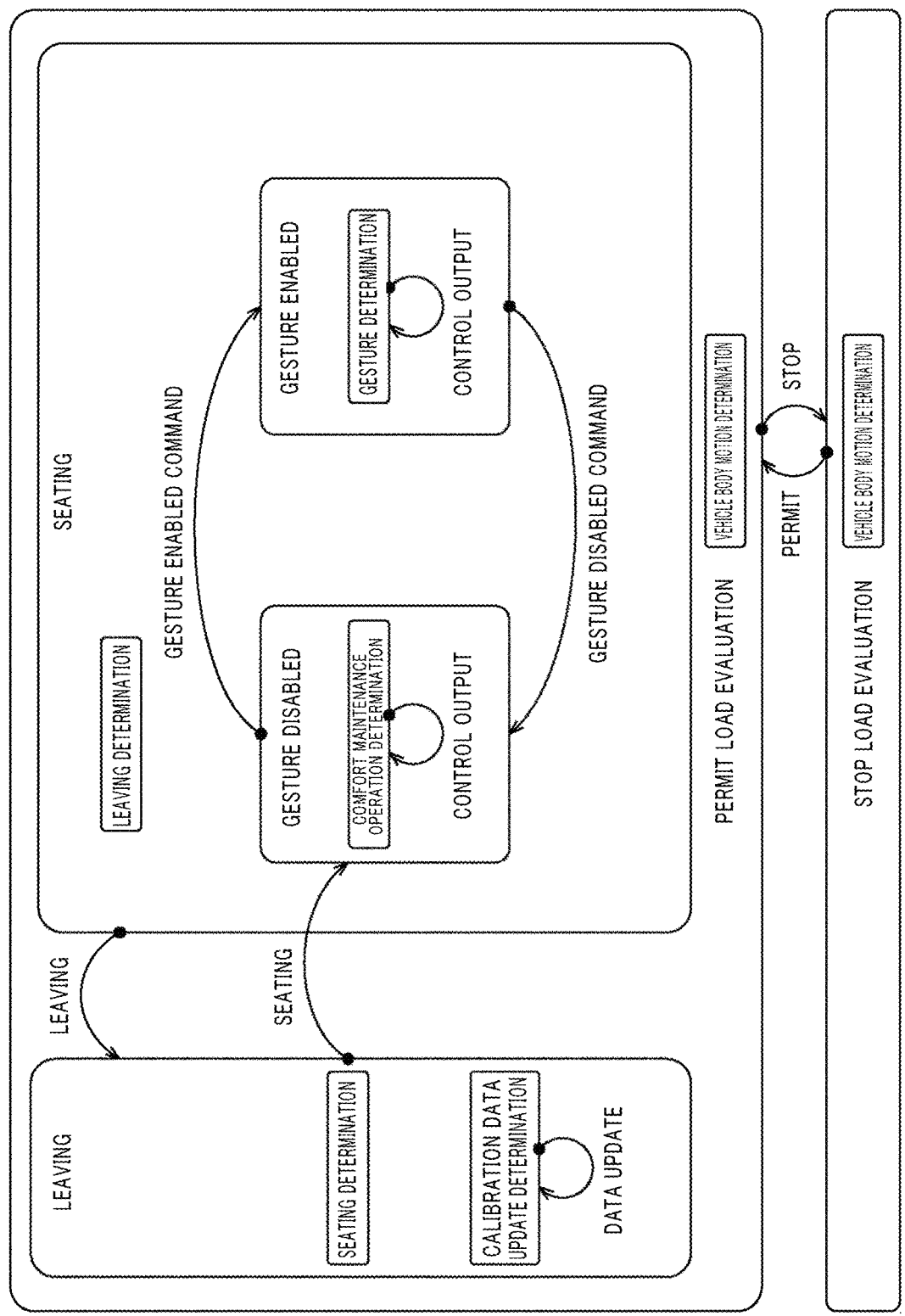
FIG. 17 illustrates an example of a state transition diagram for explaining seat movable part control processing based on load distribution changes in the case of adopting a switch mode.

FIG. 17 illustrates a state transition diagram for explaining the seat movable part control processing based on load distribution changes in the case of adopting a switch mode.

First, in the control processing device 11, a load evaluation permitted state in which load evaluation based on the pressure distribution data measured by the pressure distribution measurement unit 12 is permitted and a load evaluation stop state in which the load evaluation is stopped are set.

For example, the vehicle body motion measurement unit 20 performs vehicle body motion determination processing (refer to flowcharts of FIGS. 25 and 26) according to vehicle motion data obtained by measuring the motion of the vehicle 51, so that a transition between the load evaluation permitted state and the load evaluation stop state is performed according to the determination result. Specifically, when the vehicle body motion measurement unit 20 determines that the vehicle 51 is in motion in the load evaluation stop state, a transition from the load evaluation stop state to the load evaluation permitted state is performed. On the other hand, when the vehicle body motion measurement unit 20 determines that the vehicle 51 is not in motion in the load evaluation stop state, a transition from the load evaluation permitted state to the load evaluation stop state is performed.

Further, in the control processing device 11, in the load evaluation permitted state, a seating state in which an occupant is seated on the seat 61 of the vehicle 51 and a leaving state in which the occupant has left the seat 61 of the vehicle 51 are set.

For example, in the leaving state, the body load determination unit 18 performs seating determination processing (refer to a flowchart of FIG. 19) for determining whether or not the occupant is seated on the seat 61 of the vehicle 51. Then, when the body load determination unit 18 determines that the occupant is seated on the seat 61 of the vehicle 51, a transition from the leaving state to the seating state (a gesture disabled state thereof) is performed.

Further, in the leaving state, the load change statistical processing unit 13 performs calibration data update determination processing (refer to a flowchart of FIG. 24) for obtaining a correction value for performing zero-point correction.

On the other hand, in the seating state, the body load determination unit 18 performs leaving determination processing (refer to a flowchart of FIG. 20) for determining whether or not the occupant has left the seat 61 of the vehicle 51. Then, when the body load determination unit 18 determines that the occupant has left the seat 61 of the vehicle 51, a transition from the seating state to the leaving state is performed.

Further, in the control processing device 11, in the seating state, a gesture enabled state in which the gesture by the occupant seated on the seat 61 of the vehicle 51 is enabled and a gesture disabled state in which the gesture is disabled are set.

For example, the gesture input determination unit 17 in the gesture disabled state shifts to the gesture enabled state in response to an input of a gesture enabled command through an operation input on a button (not illustrated), and the gesture input determination unit 17 in the gesture enabled state shifts to the gesture disabled state in response to an input of a gesture disabled command. In addition, the control processing device 11 may receive an input of the gesture enabled command or the gesture disabled command by, for example, a press of a part of the pressure sensor provided on the seat 61, detection of the line of sight of the occupant gazing at a predetermined location, and recognition of a voice of the occupant saying a desired command.

In the gesture-disabled state, the body load determination unit 18 performs comfort maintenance operation determination processing (refer to a flowchart of FIG. 31) to cause the seat control unit 22 to control the operation outputs for the movable parts of the seat 61 so as to turn the seat 61 into a form that relieves physical fatigue of the occupant.

In the gesture enabled state, the gesture input determination unit 17 performs gesture determination processing (refer to a flowchart in FIG. 27) to cause the seat control unit 22 to control the operation outputs for the movable parts of the seat 61 so as to turn the seat 61 into a form corresponding to the gesture of the occupant.

In this way, for the gesture disabled state, the seat movable part control processing based on load distribution changes in the case of adopting the switch mode makes it possible to control the seat 61 so as to turn the seat 61 into a form that relieves physical fatigue of the occupant, according to an unconscious behavior of the occupant. Further, for the gesture enabled state, the seat movable part control processing makes it possible to control the seat 61 so as to turn the seat 61 into a form corresponding to the gesture of the occupant, according to a conscious behavior of the occupant. Therefore, the control processing device 11 captures the conscious or unconscious behavior of the occupant as an input and provides a function according to the input, thereby making it possible to improve convenience.

Figure 18:
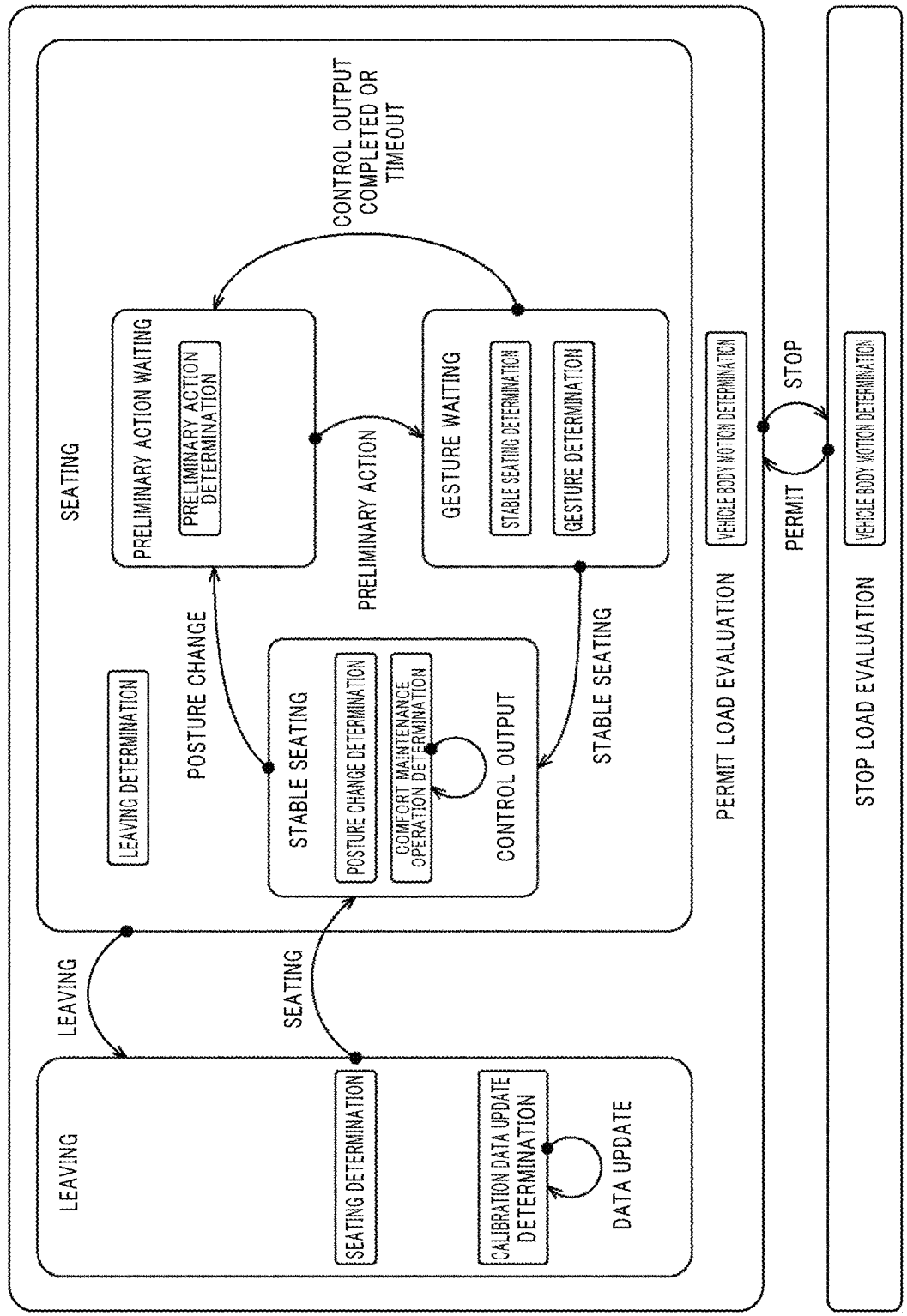
FIG. 18 illustrates an example of a state transition diagram for explaining seat movable part control processing based on load distribution changes in the case of adopting a preliminary action mode.

FIG. 18 illustrates a state transition diagram for explaining the seat movable part control processing based on load distribution changes in the case of adopting a preliminary action mode. Note that, in the state transition in the preliminary action mode illustrated in FIG. 18, description of states and processing common to the state transition in the switch mode described above with reference to FIG. 17 will be omitted.

Figure 24:
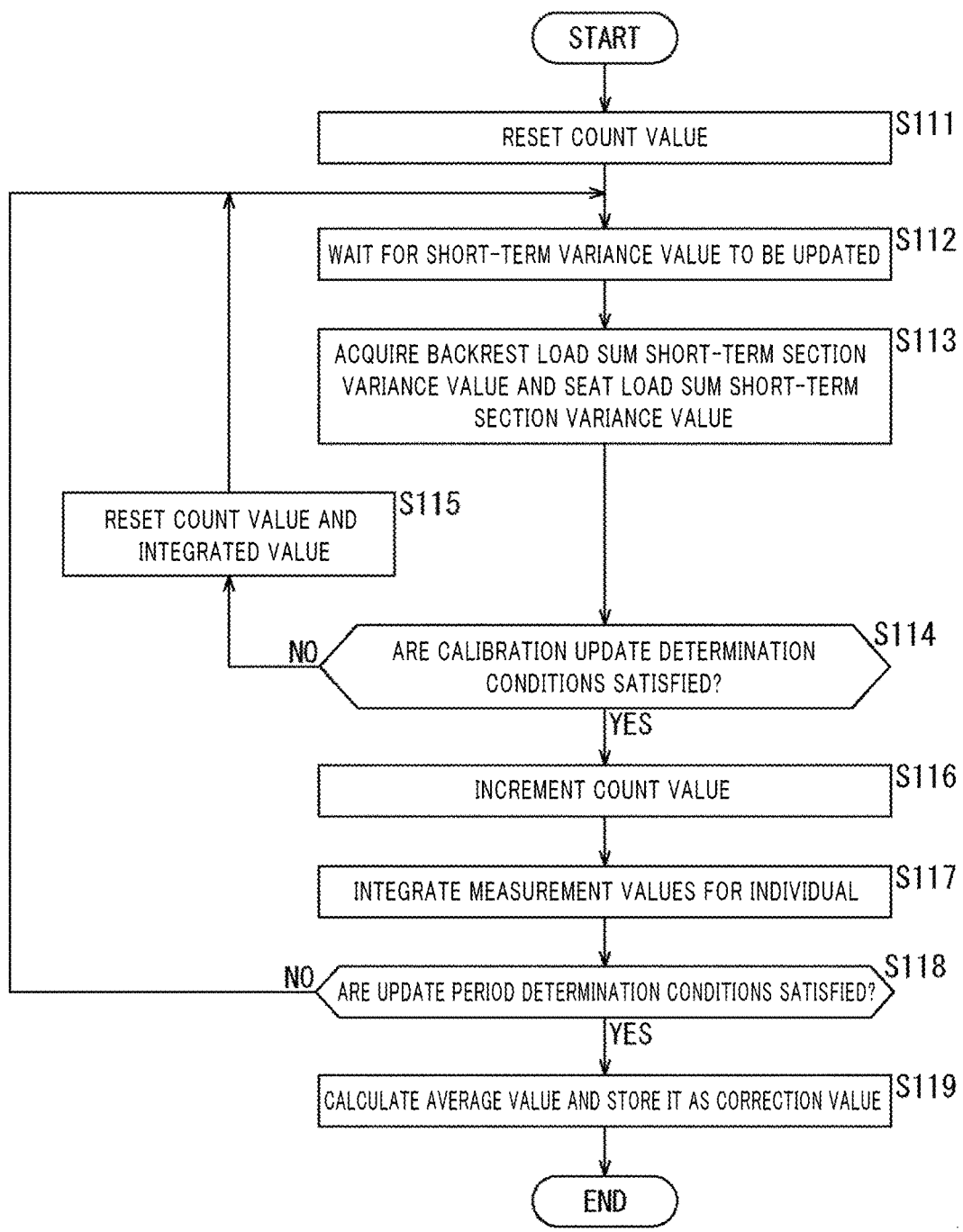
FIG. 24 is a flowchart illustrating calibration data update determination processing.
Figure 25:
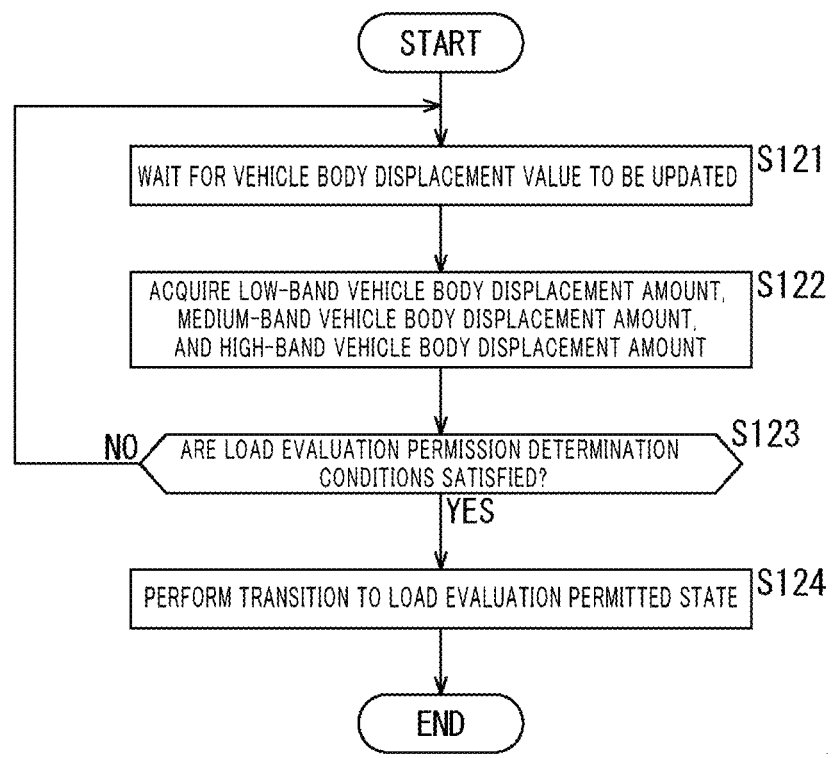
FIG. 25 is a flowchart illustrating body motion determination in a load evaluation stop state.
Figure 26:
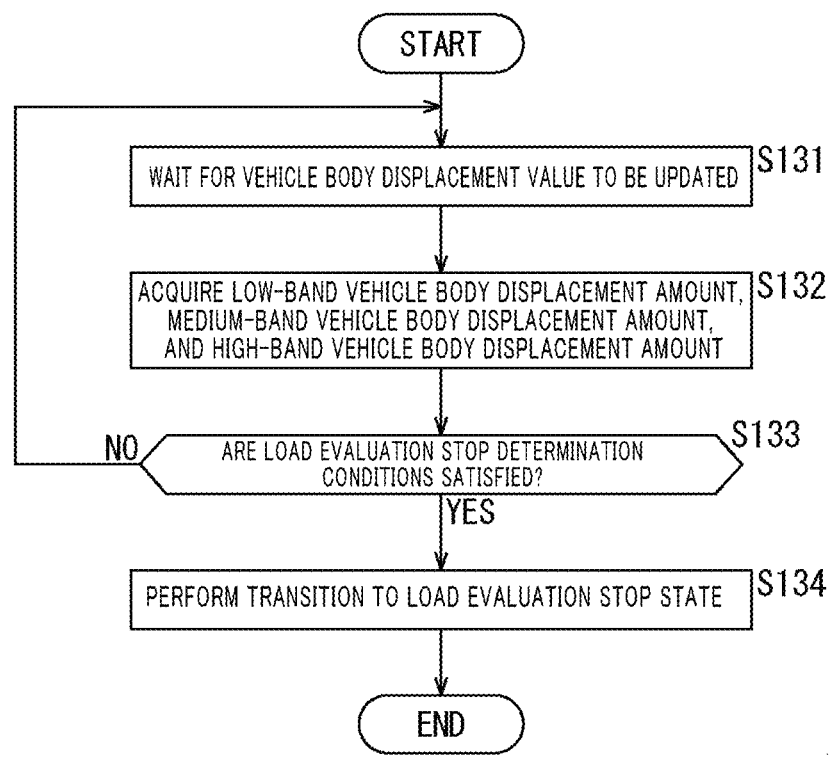
FIG. 26 is a flowchart illustrating body motion determination in a load evaluation permitted state.

Specifically, in the seat movable part control processing based on load distribution changes in the case of adopting the preliminary action mode, transition between the load evaluation permitted state and the load evaluation stop state is performed based on vehicle body motion determination (refer to flowcharts of FIGS. 25 and 26). Further, in the leaving state, the seating determination processing (refer to the flowchart of FIG. 19) and calibration data update determination (see the flowchart of FIG. 24) are performed, and when it is determined that the occupant is seated, a transition from the leaving state to the seating state (a stable seating state thereof) is performed. Further, in the seating state, the leaving determination processing (refer to the flowchart of FIG. 20) is performed.

Then, in the seat movable part control processing based on load distribution changes in the case of adopting the preliminary action mode, a stable seating state, a preliminary action waiting state, and a gesture waiting state are set in the seating state.

In the stable seating state, the body load determination unit 18 performs the comfort maintenance operation determination processing (refer to the flowchart of FIG. 31) to cause the seat control unit 22 to control the operation outputs for the movable parts of the seat 61 so as to turn the seat 61 into a form that relieves physical fatigue of the occupant.

Further, in the stable seating state, the gesture input determination unit 17 performs posture change determination processing (refer to a flowchart of FIG. 22), and when the gesture input determination unit 17 determines that the posture of the occupant seated on the seat 61 of the vehicle 51 has not changed, the gesture input determination unit 17 maintains the stable seating state. On the other hand, when the gesture input determination unit 17 determines that the posture of the occupant seated on the seat 61 of the vehicle 51 is changed, a transition from the stable seating state to the preliminary action waiting state is performed.

In the preliminary action waiting state, the gesture input determination unit 17 performs preliminary motion determination processing (refer to a flowchart of FIG. 23) to maintain the preliminary action waiting state until a preliminary motion is performed. For example, since the occupant may temporarily stop his/her behavior before the occupant makes a gesture input, such stop of behavior can be detected as a preliminary action. Then, when the gesture input determination unit 17 determines that the preliminary action is performed, a transition from the preliminary action waiting state to the gesture waiting state is performed.

In the gesture waiting state, the gesture input determination unit 17 performs stable seating determination processing (refer to a flowchart of FIG. 21), and when the gesture input determination unit 17 determines that the posture of the occupant seated on the seat 61 of the vehicle 51 is stable, a transition from the gesture waiting state to the stable seating state is performed.

Further, in the gesture waiting state, the gesture input determination unit 17 performs the gesture determination processing (refer to the flowchart in FIG. 27), and determines that the gesture is performed to cause the seat control unit 22 to control the operation outputs for the movable parts of the seat 61 so as to turn the seat 61 into a form corresponding to the gesture of the occupant. Then, when the control of the operation outputs according to the gesture is completed, a transition from the gesture waiting state to the preliminary action waiting state is performed. Alternatively, when it is determined that neither the gesture has been performed nor the posture of the occupant is stable during the predetermined waiting time, a timeout occurs and a transition from the gesture waiting state to the preliminary action waiting state is performed.

In this way, in the seat movable part control processing based on load distribution changes in the case of adopting the preliminary motion mode, the gesture determination is performed when a preliminary motion in which the occupant tries to perform a gesture input is detected. Therefore, the occupant can smoothly perform the gesture without performing a special operation (e.g., an operation on a switch) for performing the gesture input, thereby making it possible to highly improve the convenience.

Figure 19:
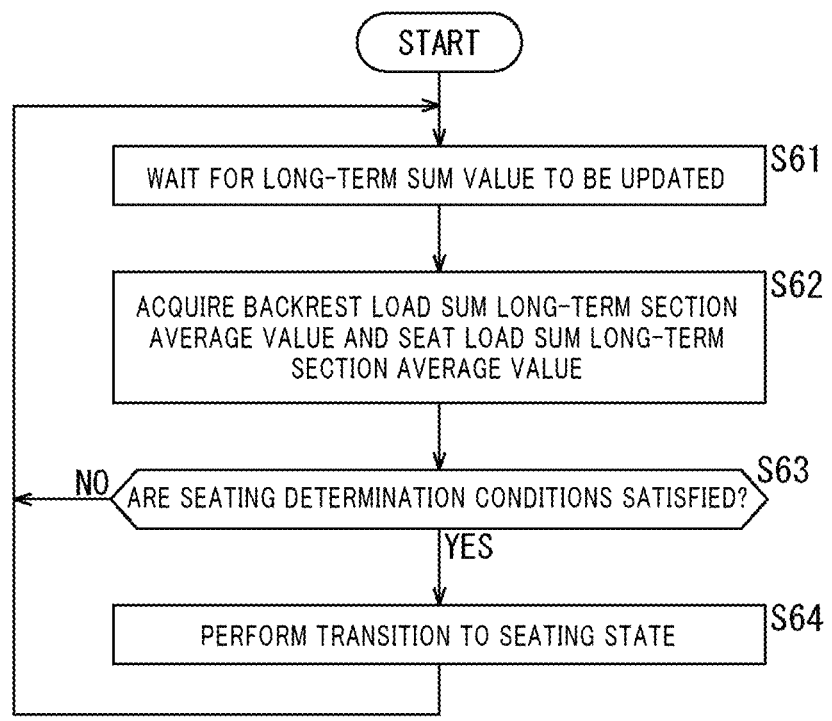
FIG. 19 is a flowchart illustrating seating determination processing.

The seating determination processing performed in the leaving state illustrated in FIGS. 17 and 18 will be described with reference to the flowchart illustrated in FIG. 19.

Figure 14:
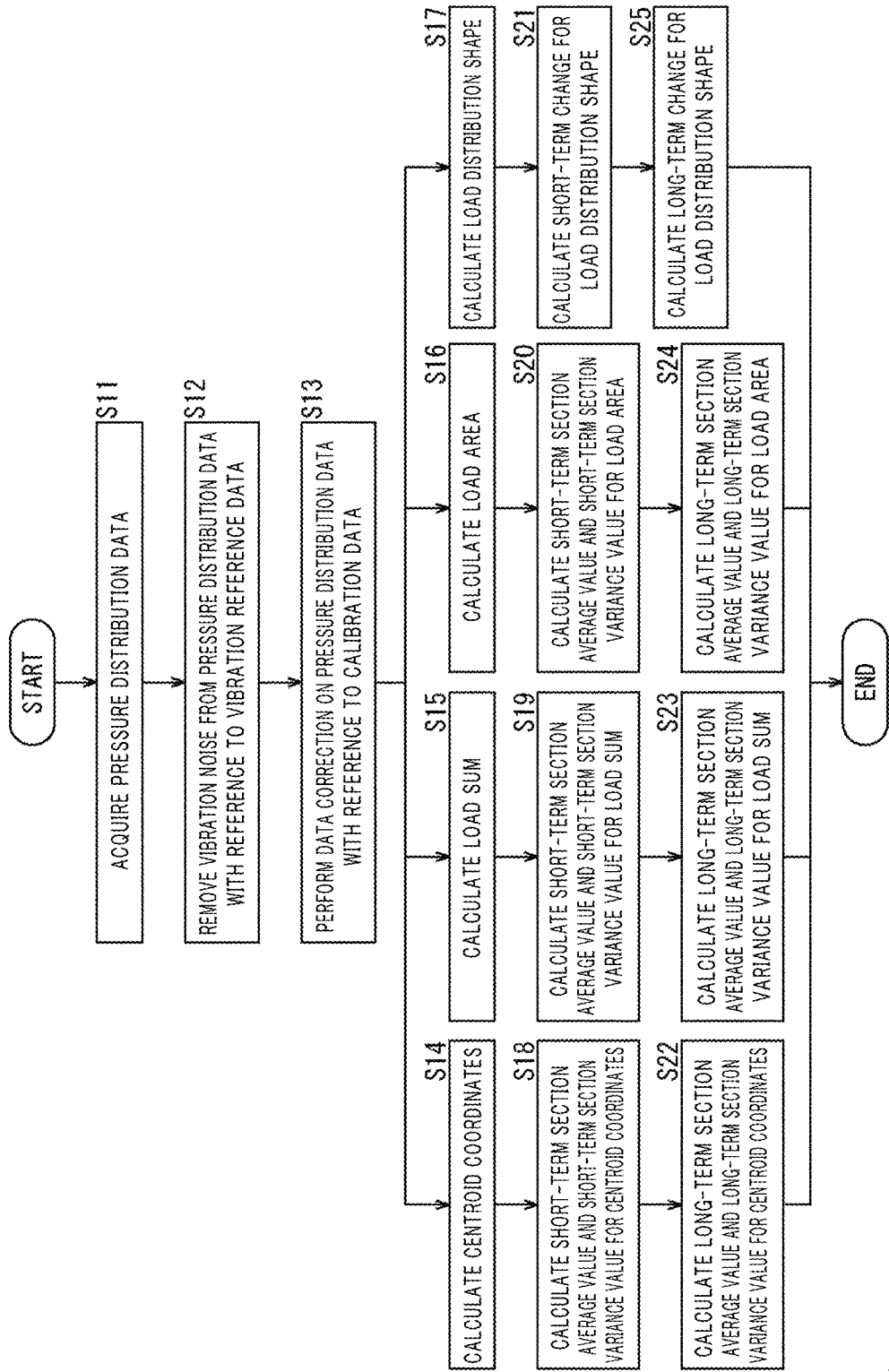
FIG. 14 is a flowchart illustrating pressure distribution measurement processing and load change statistical processing.

In step S61, the body load determination unit 18 waits for the long-term sum value to be updated by the load change statistical processing unit 13 performing the processing of steps S22 to S24 of FIG. 14. Then, when the long-term sum value is supplied from the load change statistical processing unit 13 to the body load determination unit 18, the processing proceeds to step S62.

In step S62, the body load determination unit 18 acquires a backrest load sum long-term section average value LAve_Wsum_BR and a seat load sum long-term section average value LAve_Wsum_SE from among the long-term sum values supplied from the load change statistical processing unit 13 in step S61.

In step S63, the body load determination unit 18 uses determination parameters (predetermined specified values) to determine whether or not the backrest load sum long-term section average value LAve_Wsum_BR and the seat load sum long-term section average value LAve_Wsum_SE acquired in step S62 satisfy seating determination conditions.

For example, when the backrest load sum long-term section average value LAve_Wsum_BR is larger than a backrest seating load sum determination parameter COND_DW_BR, and the seat load sum long-term section average value LAve_Wsum_SE is larger than a seat seating load sum determination parameter COND_DW_SE, the body load determination unit 18 determines that the seating determination conditions are satisfied.

That is, when the following are both TRUE:
LAve_Wsum_BR>COND_DW_BR
LAve_Wsum_SE>COND_DW_SE,
the body load determination unit 18 determines that the seating determination conditions are satisfied.

When the body load determination unit 18 determines in step S63 that the seating determination conditions are satisfied, the processing proceeds to step S64, a transition from the leaving state to the seating state is performed, and then the processing returns to step S61.

On the other hand, when the body load determination unit 18 determines in step S63 that the seating determination conditions are not satisfied, the processing returns to step S61, and then the same processing is repeated thereafter.

As described above, in the seating determination processing, since the seating determination is performed based on both the backrest load sum long-term section average value LAve_Wsum_BR and the seat load sum long-term section average value LAve_Wsum_SE, it is possible to more reliably detect that the occupant is seated on the seat 61.

Figure 20:
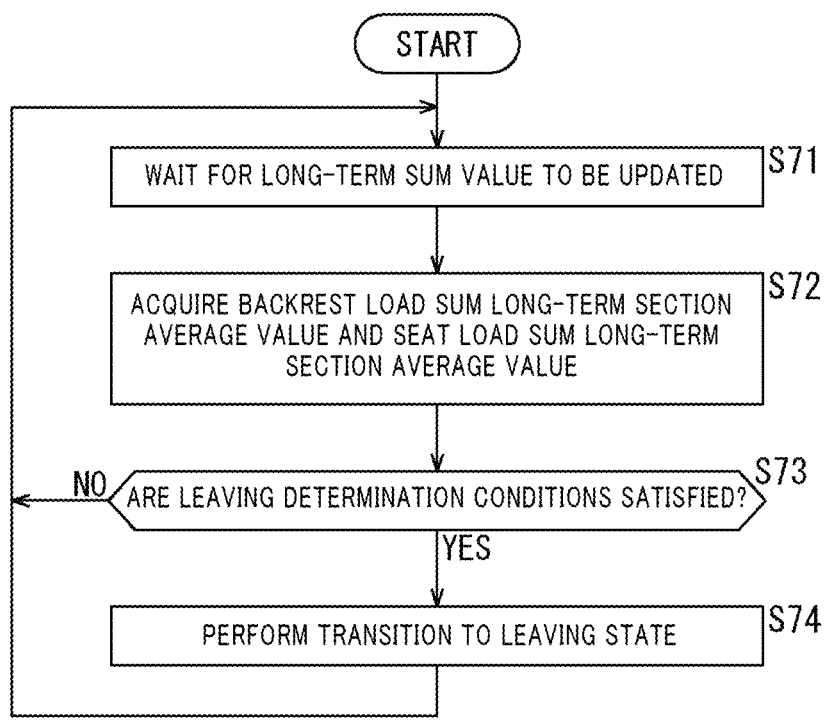
FIG. 20 is a flowchart illustrating leaving determination processing.

The leaving determination processing performed in the seating state illustrated in FIGS. 17 and 18 will be described with reference to the flowchart illustrated in FIG. 20.

In step S71, the body load determination unit 18 waits for the long-term sum value to be updated by the load change statistical processing unit 13 performing the processing of steps S22 to S24 of FIG. 14. Then, when the long-term sum value is supplied from the load change statistical processing unit 13 to the body load determination unit 18, the processing proceeds to step S72.

In step S72, the body load determination unit 18 acquires a backrest load sum long-term section average value LAve_Wsum_BR and a seat load sum long-term section average value LAve_Wsum_SE from among the long-term sum values supplied from the load change statistical processing unit 13 in step S71.

In step S73, the body load determination unit 18 uses determination parameters (predetermined specified values) to determine whether or not the backrest load sum long-term section average value LAve_Wsum_BR and the seat load sum long-term section average value LAve_Wsum_SE acquired in step S72 satisfy leaving determination conditions.

For example, when the backrest load sum long-term section average value LAve_Wsum_BR is smaller than a backrest leaving load sum determination parameter COND_UP_BR, and the seat load sum long-term section average value LAve_Wsum_SE is smaller than a seat leaving load sum determination parameter COND_UP_SE, the body load determination unit 18 determines that the leaving determination conditions are satisfied.

That is, when the following are both TRUE:
LAve_Wsum_BR<COND_UP_BR
LAve_Wsum_SE<COND_UP_SE,
the body load determination unit 18 determines that the leaving determination conditions are satisfied.

When the body load determination unit 18 determines in step S73 that the leaving determination conditions are satisfied, the processing proceeds to step S74, a transition from the seating state to the leaving state is performed, and then the processing returns to step S71.

On the other hand, when the body load determination unit 18 determines in step S73 that the leaving determination conditions are not satisfied, the processing returns to step S71, and then the same processing is repeated.

As described above, in the leaving determination processing, since the leaving determination is performed based on both the backrest load sum long-term section average value LAve_Wsum_BR and the seat load sum long-term section average value LAve_Wsum_SE, it is possible to more reliably detect that the occupant has left the seat 61.

Figure 21:
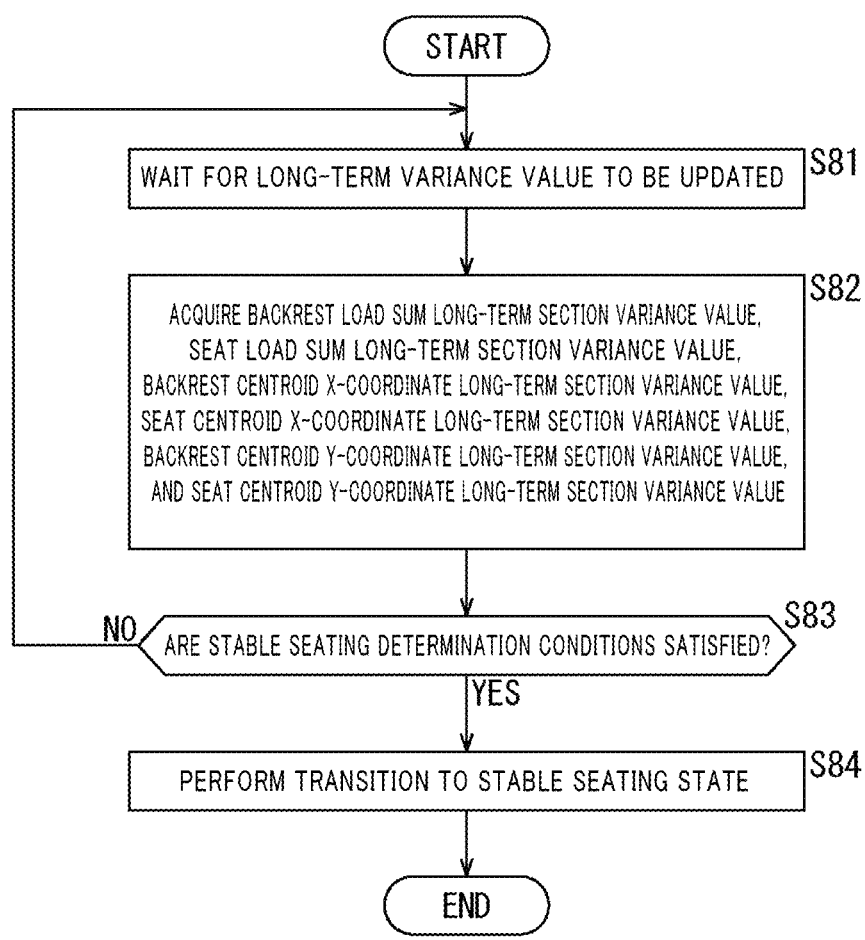
FIG. 21 is a flowchart illustrating stable seating determination processing.

The stable seating determination processing performed in the gesture waiting state illustrated in FIG. 18 will be described with reference to the flowchart illustrated in FIG. 21.

In step S81, the gesture input determination unit 17 waits for the long-term variance value to be updated by the load change statistical processing unit 13 performing the processing of steps S22 to S24 of FIG. 14. Then, when the long-term variance value is supplied from the load change statistical processing unit 13 to the gesture input determination unit 17, the processing proceeds to step S82.

In step S82, the gesture input determination unit 17 acquires, from among the long-term variance values supplied from the load change statistical processing unit 13 in step S81, a backrest load sum long-term section variance value LS2_Wsum_BR, a seat load sum long-term section variance value LS2_Wsum_SE, a backrest centroid x-coordinate long-term section variance value LS2_Cx_BR, a seat centroid x-coordinate long-term section variance value LS2_Cx_SE, a backrest centroid y-coordinate long-term section variance value LS2_Cy_BR, and a seat centroid y-coordinate long-term section variance value LS2_Cy_SE.

In step S83, the gesture input determination unit 17 uses determination parameters (predetermined specified values) to determine whether or not the backrest load sum long-term section variance value LS2_Wsum_BR, the seat load sum long-term section variance value LS2_Wsum_SE, the backrest centroid x-coordinate long-term section variance value LS2_Cx_BR, the seat centroid x-coordinate long-term section variance value LS2_Cx_SE, the backrest centroid y-coordinate long-term section variance value LS2_Cy_BR, and the seat centroid y-coordinate long-term section variance value LS2_Cy_SE, which are acquired in step S82, satisfy stable seating determination conditions.

For example, when the backrest load sum long-term section variance value LS2_Wsum_BR is smaller than a backrest stable seating load sum determination parameter COND_STBL_Wsum_BR, the seat load sum long-term section variance value LS2_Wsum_SE is smaller than a seat stable seating load sum determination parameter COND_STBL_Wsum_SE, the backrest centroid x-coordinate long-term section variance value LS2_Cx_BR is smaller than a backrest stable seating centroid x-coordinate determination parameter COND_STBL_Cx_BR, the seat centroid x-coordinate long-term section variance value LS2_Cx_SE is smaller than a seat stable seating centroid x-coordinate determination parameter COND_STBL_Cx_SE, the backrest centroid y-coordinate long-term section variance value LS2_Cy_BR is smaller than a backrest stable seating centroid y-coordinate determination parameter COND_STBL_Cy_BR, and the seat centroid y-coordinate long-term section variance value LS2_Cy_SE is smaller than a seat stable seating centroid y-coordinate determination parameter COND_STBL_Cy_SE, the gesture input determination unit 17 determines that the stable seating determination conditions are satisfied.

That is, when the following are all TRUE:
LS2_Wsum_BR<COND_STBL_Wsum_BR
LS2_Wsum_SE<COND_STBL_Wsum_SE
LS2_Cx_BR<COND_STBL_Cx_BR
LS2_Cx_SE<COND_STBL_Cx_SE
LS2_Cy_BR<COND_STBL_Cy_BR
LS2_Cy_SE<COND_STBL_Cy_SE,
the gesture input determination unit 17 determines that the stable seating determination conditions are satisfied.

When the gesture input determination unit 17 determines in step S83 that the stable seating determination conditions are satisfied, the processing proceeds to step S84, a transition from the gesture waiting state to the stable seating state is performed, and then the processing ends.

On the other hand, when the gesture input determination unit 7 determines in step S83 that the stable seating determination conditions are not satisfied, the processing returns to step S81, and then the same processing is repeated.

As described above, in the stable seating determination processing, since the stable seating determination is performed based on all of the backrest load sum long-term section variance value LS2_Wsum_BR, the seat load sum long-term section variance value LS2_Wsum_SE, the backrest centroid x-coordinate long-term section variance value LS2_Cx_BR, the seat centroid x-coordinate long-term section variance value LS2_Cx_SE, the backrest centroid y-coordinate long-term section variance value LS2_Cy_BR, and the seat centroid y-coordinate long-term section variance value LS2_Cy_SE, it is possible to more reliably detect that the occupant is stably seated on the seat 61.

Figure 22:
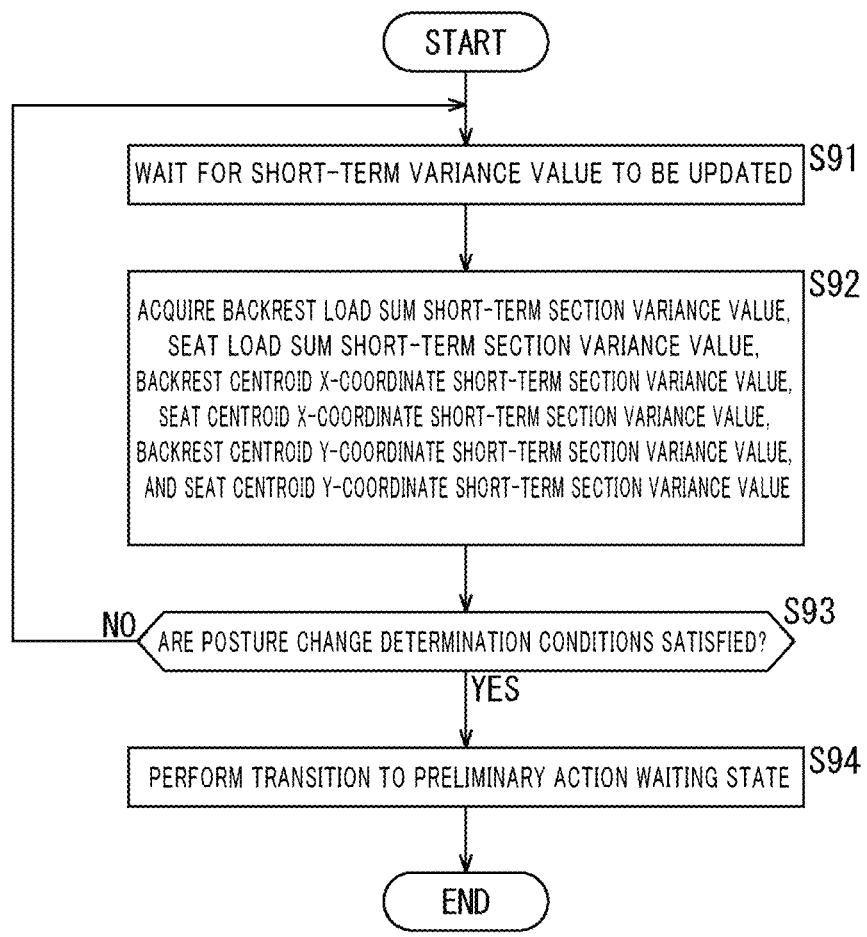
FIG. 22 is a flowchart illustrating posture change determination processing.

The posture change determination processing performed in the stable seating state illustrated in FIG. 18 will be described with reference to the flowchart illustrated in FIG. 22.

In step S91, the gesture input determination unit 17 waits for the short-term variance value to be updated by the load change statistical processing unit 13 performing the processing of steps S18 to S20 of FIG. 14. Then, when the short-term variance value is supplied from the load change statistical processing unit 13 to the gesture input determination unit 17, the processing proceeds to step S92.

In step S92, the gesture input determination unit 17 acquires, from among the short-term variance values supplied from the load change statistical processing unit 13 in step S91, a backrest load sum short-term section variance value SS2_Wsum_BR, a seat load sum short-term section variance value SS2_Wsum_SE, a backrest centroid x-coordinate short-term section variance value SS2_Cx_BR, a seat centroid x-coordinate short-term section variance value SS2_Cx_SE, a backrest centroid y-coordinate short-term section variance value SS2_Cy_BR, and a seat centroid y-coordinate short-term section variance value SS2_Cy_SE.

In step S93, the gesture input determination unit 17 uses determination parameters (predetermined specified values) to determine whether or not the backrest load sum short-term section variance value SS2_Wsum_BR, the seat load sum short-term section variance value SS2_Wsum_SE, the backrest centroid x-coordinate short-term section variance value SS2_Cx_BR, the seat centroid x-coordinate short-term section variance value SS2_Cx_SE, the backrest centroid y-coordinate short-term section variance value SS2_Cy_BR, and the seat centroid y-coordinate short-term section variance value SS2_Cy_SE, which are acquired in step S92, satisfy posture change determination conditions.

For example, when any one of the following is satisfied: the backrest load sum short-term section variance value SS2_Wsum_BR being larger than a backrest posture change determination parameter COND_ACT_Wsum_BR; the seat load sum short-term section variance value SS2_Wsum_SE being larger than a seat posture change load sum determination parameter COND_ACT_Wsum_SE; the backrest centroid x-coordinate short-term section variance value SS2_Cx_BR being larger than a backrest posture change centroid x-coordinate determination parameter COND_ACT_Cx_BR; the seat centroid x-coordinate short-term section variance value SS2_Cx_SE being larger than a seat posture change centroid x-coordinate determination parameter COND_ACT_Cx_SE; the backrest centroid y-coordinate short-term section variance value SS2_Cy_BR being larger than a backrest posture change centroid y-coordinate determination parameter COND_ACT_Cy_BR; and the seat centroid y-coordinate short-term section variance value SS2_Cy_SE being larger than a seat posture change centroid y-coordinate determination parameter COND_ACT_Cy_SE, the gesture input determination unit 17 determines that the posture change determination conditions are satisfied.

That is, when any one of the following is:
SS2_Wsum_BR>COND_ACT_Wsum_BR
SS2_Wsum_SE>COND_ACT_Wsum_SE
SS2_Cx_BR>COND_ACT_Cx_BR
SS2_Cx_SE>COND_ACT_Cx_SE
SS2_Cy_BR>COND_ACT_Cy_BR
SS2_Cy_SE>COND_ACT_Cy_SE,
the gesture input determination unit 17 determines that the posture change determination conditions are satisfied.

When the gesture input determination unit 17 determines in step S93 that the posture change determination conditions are satisfied, the processing proceeds to step S94, a transition from the stable seating state to the preliminary action waiting state is performed, and then the processing ends.

On the other hand, when the gesture input determination unit 17 determines in step S93 that the posture change determination conditions are not satisfied, the processing returns to step S91, and then the same processing is repeated.

As described above, in the posture change determination processing, since the posture change determination is performed based on any one of the backrest load sum short-term section variance value SS2_Wsum_BR, the seat load sum short-term section variance value SS2_Wsum_SE, the backrest centroid x-coordinate short-term section variance value SS2_Cx_BR, the seat centroid x-coordinate short-term section variance value SS2_Cx_SE, the backrest centroid y-coordinate short-term section variance value SS2_Cy_BR, and the seat centroid y-coordinate short-term section variance value SS2_Cy_SE, it is possible to more quickly detect that the posture of the occupant is changed and then make a transition to the preliminary action waiting state.

Figure 23:
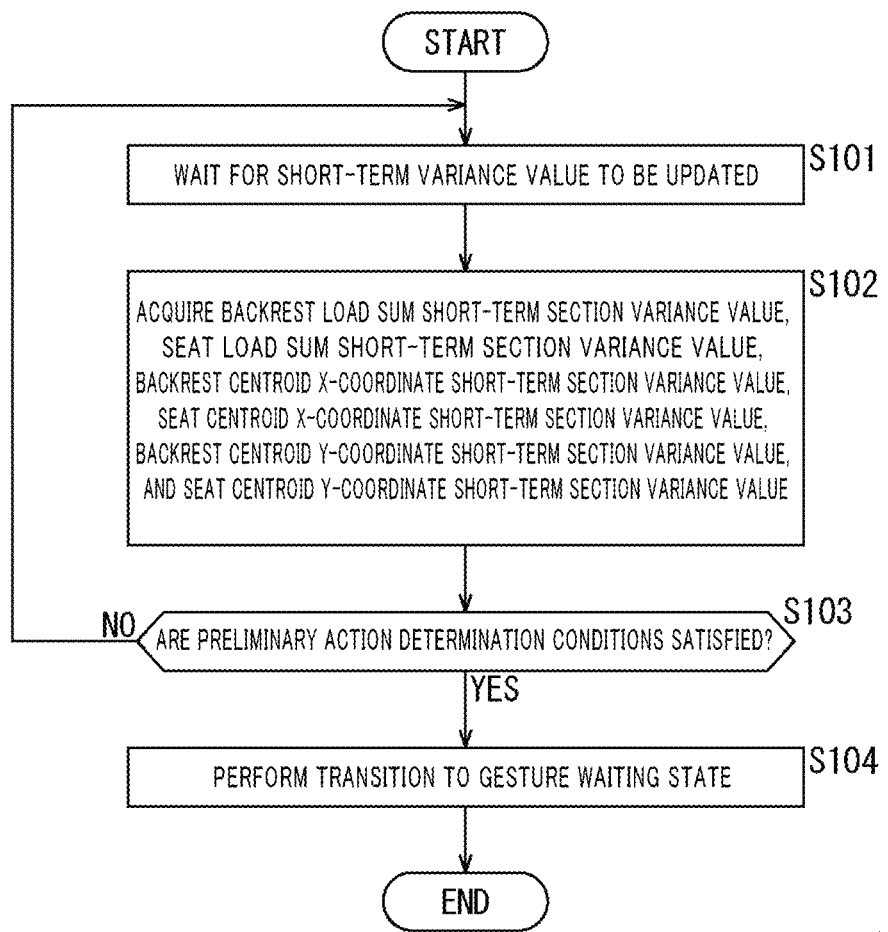
FIG. 23 is a flowchart illustrating preliminary action determination processing.

The preliminary action determination processing performed in the preliminary action waiting state illustrated in FIG. 18 will be described with reference to the flowchart illustrated in FIG. 23.

In step S101, the gesture input determination unit 17 waits for the short-term variance value to be updated by the load change statistical processing unit 13 performing the processing of steps S18 to S20 of FIG. 14. Then, when the short-term variance value is supplied from the load change statistical processing unit 13 to the gesture input determination unit 17, the processing proceeds to step S102.

In step S102, the gesture input determination unit 17 acquires, from among the short-term variance values supplied from the load change statistical processing unit 13 in step S101, a backrest load sum short-term section variance value SS2_Wsum_BR, a seat load sum short-term section variance value SS2_Wsum_SE, a backrest centroid x-coordinate short-term section variance value SS2_Cx_BR, a seat centroid x-coordinate short-term section variance value SS2_Cx_SE, a backrest centroid y-coordinate short-term section variance value SS2_Cy_BR, and a seat centroid y-coordinate short-term section variance value SS2_Cy_SE.

In step S103, the gesture input determination unit 17 uses determination parameters (predetermined specified values) to determine whether or not the backrest load sum short-term section variance value SS2_Wsum_BR, the seat load sum short-term section variance value SS2_Wsum_SE, the backrest centroid x-coordinate short-term section variance value SS2_Cx_BR, the seat centroid x-coordinate short-term section variance value SS2_Cx_SE, the backrest centroid y-coordinate short-term section variance value SS2_Cy_BR, and the seat centroid y-coordinate short-term section variance value SS2_Cy_SE, which are acquired in step S102, satisfy preliminary action determination conditions.

For example, when the backrest load sum short-term section variance value SS2_Wsum_BR is smaller than a backrest preliminary action determination parameter COND_PRE_Wsum_BR, the seat load sum short-term section variance value SS2_Wsum_SE is smaller than a seat preliminary action load sum determination parameter COND_PRE_Wsum_SE, the backrest centroid x-coordinate short-term section variance value SS2_Cx_BR is smaller than a backrest preliminary action centroid x-coordinate determination parameter COND_PRE_Cx_BR, the seat centroid x-coordinate short-term section variance value SS2_Cx_SE is smaller than a seat preliminary action centroid x-coordinate determination parameter COND_PRE_Cx_SE, the backrest centroid y-coordinate short-term section variance value SS2_Cy_BR is smaller than a backrest preliminary action centroid y-coordinate determination parameter COND_PRE_Cy_BR, and the seat centroid y-coordinate short-term section variance value SS2_Cy_SE is smaller than a seat preliminary action centroid y-coordinate determination parameter COND_PRE_Cy_SE, the gesture input determination unit 17 determines that the preliminary action determination conditions are satisfied.

That is, when the following are all TRUE:
SS2_Wsum_BR<COND_PRE_Wsum_BR
SS2_Wsum_SE<COND_PRE_Wsum_SE
SS2_Cx_BR<COND_PRE_Cx_BR
SS2_Cx_SE<COND_PRE_Cx_SE
SS2_Cy_BR<COND_PRE_Cy_BR
SS2_Cy_SE<COND_PRE_Cy_SE,
the gesture input determination unit 17 determines that the preliminary action determination conditions are satisfied.

When the gesture input determination unit 17 determines in step S103 that the preliminary action determination conditions are satisfied, the processing proceeds to step S104, a transition from the preliminary action waiting state to the gesture waiting state is performed, and then the processing ends.

On the other hand, when the gesture input determination unit 17 determines in step S103 that the preliminary action determination conditions are not satisfied, the processing returns to step S101, and then the same processing is repeated.

As described above, in the preliminary action determination processing, since the preliminary action determination is performed based on all of: the backrest load sum short-term section variance value SS2_Wsum_BR, the seat load sum short-term section variance value SS2_Wsum_SE, the backrest centroid x-coordinate short-term section variance value SS2_Cx_BR, the seat centroid x-coordinate short-term section variance value SS2_Cx_SE, the backrest centroid y-coordinate short-term section variance value SS2_Cy_BR, and the seat centroid y-coordinate short-term section variance value SS2_Cy_SE, it is possible to more reliably detect that the occupant performs a preliminary action and then make a transition to the gesture waiting state.

The calibration data update determination processing performed in the leaving state illustrated in FIGS. 17 and 18 will be described with reference to the flowchart illustrated in FIG. 24.

In step S111, the load change statistical processing unit 13 resets a count value for counting the number of times the processing is repeated (COUNT=0).

In step S112, the load change statistical processing unit 13 waits for the short-term variance value to be updated by performing the processing of steps S18 to S20 of FIG. 14, and when the short-term variance value is updated, then the processing proceeds to step S113.

In step S113, the load change statistical processing unit 13 acquires the backrest load sum short-term section variance value SS2_Wsum_BR and the seat load sum short-term section variance value SS2_Wsum_SE from among the short-term variance values updated in step S112.

In step S114, the load change statistical processing unit 13 uses determination parameters (predetermined specified values) to determine whether or not the backrest load sum short-term section variance value SS2_Wsum_BR and the seat total sum short-term variance value SS2_Wsum_SE, which are acquired in step S113, satisfy calibration update determination conditions.

For example, when the backrest load sum short-term section variance value SS2_Wsum_BR is smaller than a backrest load sum calibration update determination parameter COND_CORR_Wsum_BR, and the seat load sum short-term section variance value SS2_Wsum_SE is smaller than a seat load sum calibration update determination parameter COND_CORR_Wsum_SE, the load change statistical processing unit 13 determines that the calibration update determination conditions are satisfied.

That is, when the following are both TRUE:
SS2_Wsum_BR<COND_CORR_Wsum_BR
SS2_Wsum_SE<COND_CORR_Wsum_SE,
the load change statistical processing unit 13 determines that the calibration update determination conditions are satisfied.

When the load change statistical processing unit 13 determines in step S114 that the calibration update determination conditions are not satisfied, the processing proceeds to step S115. In step S115, the load change statistical processing unit 13 resets the count value and an integrated value (COUNT=0, AVE_Wmn=0), the processing returns to step S112, and then the same processing is repeated.

On the other hand, when the load change statistical processing unit 13 determines in step S114 that the calibration update determination conditions are satisfied, the processing roceeds to step S116.

In step S116, the load change statistical processing unit 13 increments the count value (COUNT+=1).

In step S117, the load change statistical processing unit 13 integrates measurement values for each of the individual pressure sensors to obtain the integrated value (AVE_Wmn+=AVE_Wmn).

In step S118, the load change statistical processing unit 13 determines whether or not an update period determination condition is satisfied, for example, whether or not the current count value is equal to or larger than an update period determination parameter. For example, if the short-term section S is set to 500 ms as illustrated in FIG. 8 described above and an update period is set to 10 seconds, an update period determination parameter COND_TERM_CORR is set to 20. In this case, the load change statistical processing unit 13 determines that the update period determination condition is satisfied when the current count value is equal to or larger than the update period determination parameter (COUNT≥COND_TERM_CORR).

When the load change statistical processing unit 13 determines in step S118 that the update period determination condition is not satisfied, the processing returns to step S112, and then the same processing is repeated.

On the other hand, when the load change statistical processing unit 13 determines in step S118 that the update period determination condition is satisfied, the processing proceeds to step S119.

In step S119, the load change statistical processing unit 13 calculates an average value of the integrated values finally obtained in step S117 to obtain a correction value (CORR_Wmn=AVE_Wmn/COUNT). Then, the load change statistical processing unit 13 stores, as calibration data, the correction value thus obtained, that is, the average value of the integrated values of pressure data from each pressure sensor, and then the processing ends.

As described above, when the load change statistical processing unit 13 obtains the correction, so that the pressure distribution measurement unit 12 can performs the data correction using the correction value (calibration data) supplied from the load change statistical processing unit 13. Accordingly, the pressure distribution measurement unit 12 can output accurate pressure data that has been subjected to the zero-point correction.

Note that the load change statistical processing unit 13 can also perform the same processing on the gyro sensors for which the vehicle body motion measurement unit 20 acquires the acceleration data to obtain a correction value for each gyro sensor. Then, the vehicle body motion measurement unit 20 can perform data correction using the correction value (calibration data) supplied from the load change statistical processing unit 13 in step S32 of FIG. 15 described above. Accordingly, the vehicle body motion measurement unit 20 can output accurate acceleration data that has been subjected to the zero-point correction.

The vehicle body motion determination processing performed in the load evaluation stop state illustrated in FIGS. 17 and 18 will be described with reference to the flowchart illustrated in FIG. 25.

Figure 15:
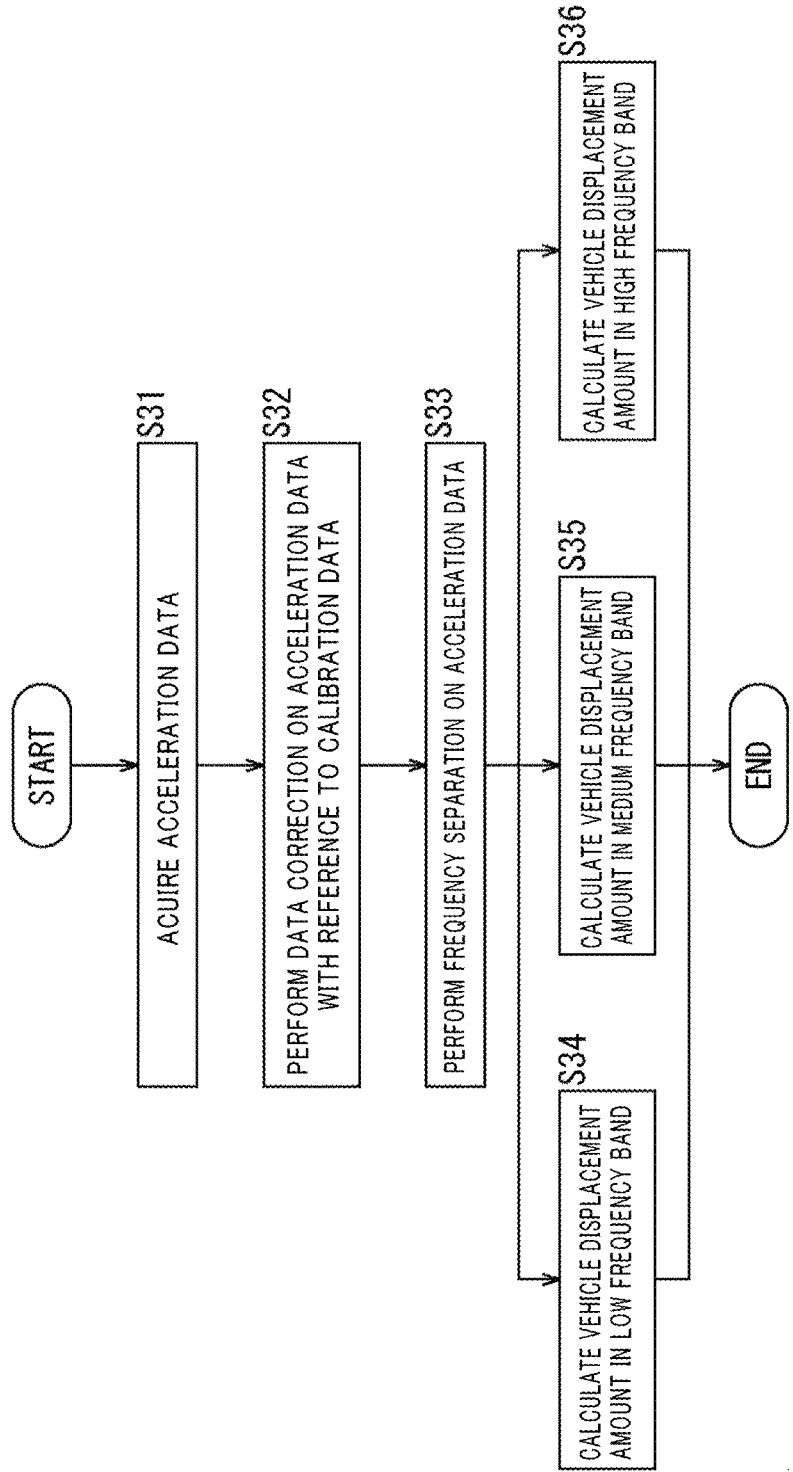
FIG. 15 is a flowchart illustrating vehicle body motion measurement processing.

In step S121, the load change statistical processing unit 13 waits for a vehicle body displacement value (vehicle motion data) to be updated by the vehicle body motion measurement unit 20 performing the processing of steps S34 to S36 of FIG. 15. Then, when the vehicle body displacement value is supplied from the vehicle body motion measurement unit 20 to the load change statistical processing unit 13, the processing proceeds to step S122.

In step S122, the load change statistical processing unit 13 acquires a low-band vehicle body displacement amount Body_LF, a medium-band vehicle body displacement amount Body_MF, and a high-band vehicle body displacement amount Body_HF from among the vehicle body displacement values supplied from the vehicle body motion measurement unit 20.

In step S123, the load change statistical processing unit 13 uses determination parameters (predetermined specified values) to determine whether or not the low-band vehicle body displacement amount Body_LF, the medium-band vehicle body displacement amount Body_MF, and the high-band vehicle body displacement amount Body_HF, which are acquired in step S122, satisfy load evaluation permission determination conditions.

For example, when the low-band vehicle body displacement amount Body_LF is smaller than a low-band vehicle body displacement amount parameter COND_Body_LF, the medium-band vehicle body displacement amount Body_MF is smaller than a medium-band vehicle body displacement amount parameter COND_Body_MF, and the high-band vehicle body displacement amount Body_HF is smaller than a high-band vehicle body displacement amount parameter COND_Body_HF, the load change statistical processing unit 13 determines that the load evaluation permission determination conditions are satisfied.

That is, when the following are both TRUE:
Body_LF<COND_Body_LF
Body_MF<COND_Body_MF
Body_HF<COND_Body_HF,
the load change statistical processing unit 13 determines that the load evaluation permission determination conditions are satisfied.

When the load change statistical processing unit 13 determines in step S123 that the load evaluation permission determination conditions are not satisfied, the processing returns to step S121, and then the same processing is repeated.

On the other hand, when the load change statistical processing unit 13 determines in step S123 that the load evaluation permission determination conditions are satisfied, the processing proceeds to step S124, a transition from the load evaluation stop state to the load evaluation permitted state, and then the processing ends.

As described above, in the vehicle body motion determination processing in the load evaluation stop state, since the vehicle body motion determination is performed based on all of the low-band vehicle body displacement amount Body_LF, the medium-band vehicle body displacement amount Body_MF, and the high-band vehicle body displacement amount Body_HF, it is possible to more reliably detect that a motion of the vehicle 51 has started.

The vehicle body motion determination processing performed in the load evaluation permitted state illustrated in FIGS. 17 and 18 will be described with reference to the flowchart illustrated in FIG. 26.

In step S131, the load change statistical processing unit 13 waits for a vehicle body displacement value (vehicle motion data) to be updated by the vehicle body motion measurement unit 20 performing the processing of steps S34 to S36 of FIG. 15. Then, when the vehicle body displacement value is supplied from the vehicle body motion measurement unit 20 to the load change statistical processing unit 13, the processing proceeds to step S132.

In step S132, the load change statistical processing unit 13 acquires a low-band vehicle body displacement amount Body_LF, a medium-band vehicle body displacement amount Body_MF, and a high-band vehicle body displacement amount Body_HF from among the vehicle body displacement values supplied from the vehicle body motion measurement unit 20.

In step S133, the load change statistical processing unit 13 uses determination parameters (predetermined specified values) to determine whether or not the low-band vehicle body displacement amount Body_LF, the medium-band vehicle body displacement amount Body_MF, and the high-band vehicle body displacement amount Body_HF, which are acquired in step S132, satisfy load evaluation stop determination conditions.

For example, when any one of the following is satisfied: the low-band vehicle body displacement amount Body_LF being smaller than a low-band vehicle body displacement amount parameter COND_Body_LF, the medium-band vehicle body displacement amount Body_MF being smaller than a medium-band vehicle body displacement amount parameter COND_Body_MF, and the high-band vehicle body displacement amount Body_HF being smaller than a high-band vehicle body displacement amount parameter COND_Body_HF, the load change statistical processing unit 13 determines that the load evaluation stop determination conditions are satisfied.

That is, when any one of the following is TRUE:
Body_LF<COND_Body_LF
Body_MF<COND_Body_MF
Body_HF<COND_Body_HF,
the load change statistical processing unit 13 determines that the load evaluation stop determination conditions are satisfied.

When the load change statistical processing unit 13 determines in step S133 that the load evaluation stop determination conditions are not satisfied, the processing returns to step S131, and then the same processing is repeated.

On the other hand, when the load change statistical processing unit 13 determines in step S133 that the load evaluation stop determination conditions are satisfied, the processing proceeds to step S134, a transition from the load evaluation permitted state to the load evaluation stop state, and then the processing ends.

As described above, in the vehicle body motion determination processing in the load evaluation stop state, since the vehicle body motion determination is performed based on any one of: the low-band vehicle body displacement amount Body_LF, the medium-band vehicle body displacement amount Body_MF, and the high-band vehicle body displacement amount Body_HF, it is possible to more reliably detect that a motion of the vehicle 51 has stopped.

The gesture determination processing performed in the gesture enabled state illustrated in FIG. 17 or in the gesture waiting state illustrated in FIG. 18 will be described with reference to the flowchart illustrated in FIG. 27.

In step S141, the gesture input determination unit 17 waits for the pressure distribution data that is centroid trajectory data (i.e., changes in load distribution shape in the short-term section S and the long-term section L) to be updated by the load change statistical processing unit 13 performing the processing of steps S21 and S25 of FIG. 14, and acquires the updated pressure distribution data.

In step S142, the gesture input determination unit 17 determines whether or not the gesture based on the pressure distribution data acquired in step S141 matches a preset gesture or a learned gesture.

When the gesture input determination unit 17 determines in step S142 that the gesture based on the pressure distribution data acquired in step S141 matches it, the processing proceeds to step S143.

In step S143, the gesture input determination unit 17 stops the stable seating determination processing that is being performed in the gesture waiting state.

In step S144, the gesture input determination unit 17 supplies, to the seat control unit 22, gesture input information according to the preset gesture or the learned gesture determined to match in step S142. In response to this, the seat control unit 22 outputs a seat control instruction according to the gesture input information to the seat 61, and controls various operation outputs for the movable parts of the seat 61.

In step S145, the seat control unit 22 waits for the movable parts of the seat 61 operating according to the seat control instruction in step S144 and accordingly stop determination data indicating that their operations are stopped being updated in the seat 61. Then, when the seat control unit 22 acquires the updated stop determination data, the processing proceeds to step S146.

In step S146, the seat control unit 22 determines based on the stop determination data acquired in step S145 whether or not the stop determination data meets the stop condition in the seat control instruction.

When the seat control unit 22 determines in step S146 that the stop condition is not met, and the processing returns to step S145 to wait for the stop determination data to be updated.

On the other hand, when the seat control unit 22 determines in step S146 that the stop condition is met, and the processing proceeds to step S147 to output the seat control stop to the seat 61.

In step S148, a transition from the gesture waiting state to the preliminary action waiting state is performed, and then the processing ends. On the other hand, when the gesture input determination unit 17 determines in step S142 that the gesture based on the pressure distribution data acquired in step S141 do not meet it, or when a time-out occurs, then the processing ends.

Figure 29:
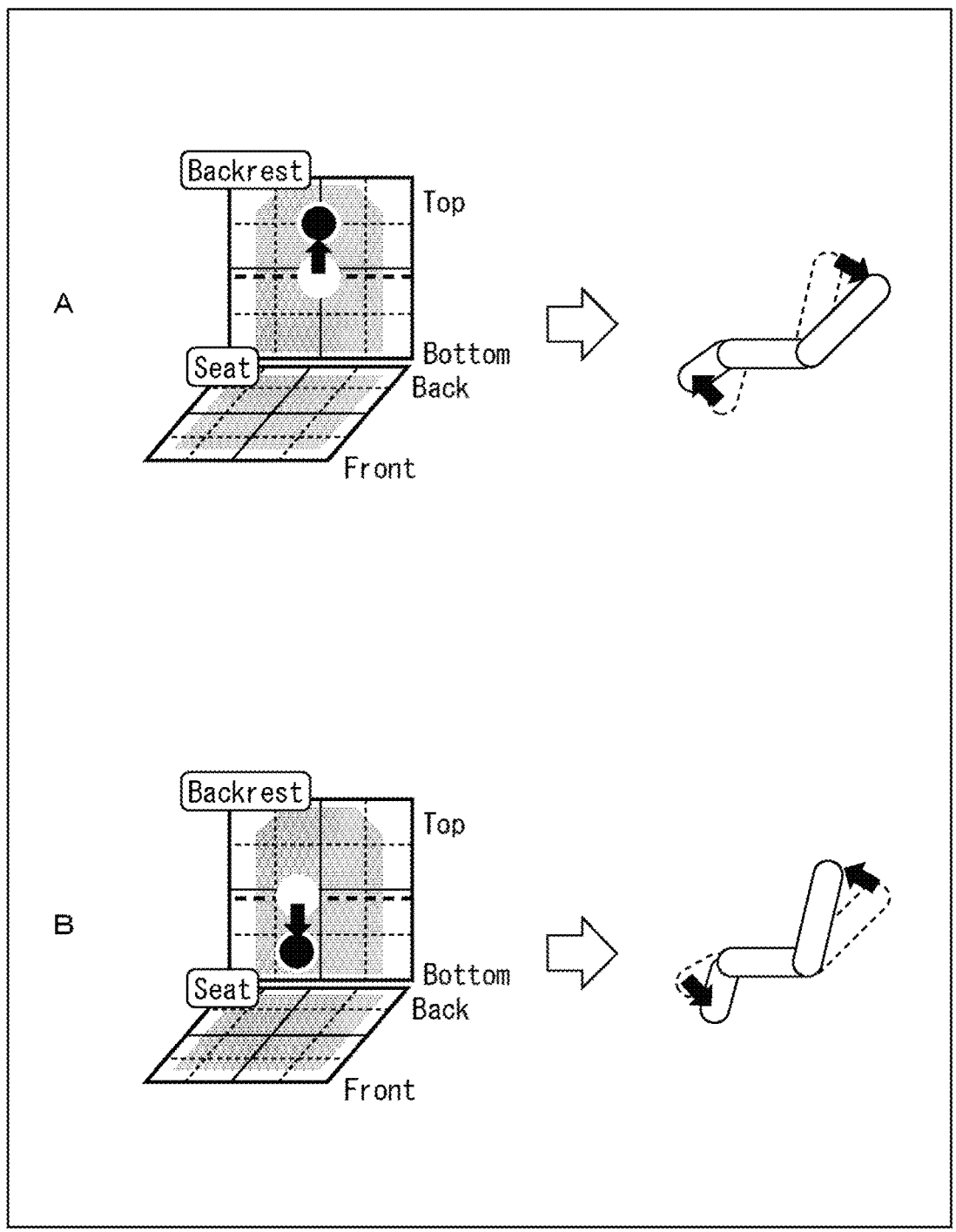
FIG. 29 is a figure which illustrates examples of operation output with respect to a backrest part.

Referring to FIGS. 28 and 29, examples of preset gestures and operation outputs are illustrated.

As a first gesture example, a gesture for instructing an operation output for reclining/raising the seatback is preset. With the operation output for reclining the seatback, as illustrated in A of FIG. 29, an operation is performed in which the footrest part 65 is raised in conjunction with the backrest part 63 being reclined. With the operation output for raising the seatback, as illustrated in B of FIG. 29, an operation is performed in which the footrest part 65 is lowered in conjunction with the backrest part 63 being raised.

For example, when it is detected that a gesture image as illustrated in FIG. 28 is performed in accordance with the corresponding determination condition, an operation output for reclining/raising the seatback is performed. Then, the operation output is stopped in accordance with the corresponding determination condition for stopping the operation output for reclining/raising the seatback.

As a second gesture example, a gesture for instructing an operation output for raising/lowering the footrest part 65 is preset. For example, when it is detected that a gesture image as illustrated in FIG. 28 is performed in accordance with the corresponding determination condition, an operation output for raising/lowering the footrest part 65 is performed. Then, the operation output is stopped in accordance with the corresponding determination condition for stopping the operation output for raising/lowering the footrest part 65.

As a third gesture example, a gesture for instructing an operation output for moving the seat surface part 64 forward/backward is preset. For example, when it is detected that a gesture image as illustrated in FIG. 28 is performed in accordance with the corresponding determination condition, an operation output for moving the seat surface part 64 forward/backward is performed. Then, the operation output is stopped in accordance with the corresponding determination condition for stopping the operation output for moving the seat surface part 64 forward/backward.

Figure 30:
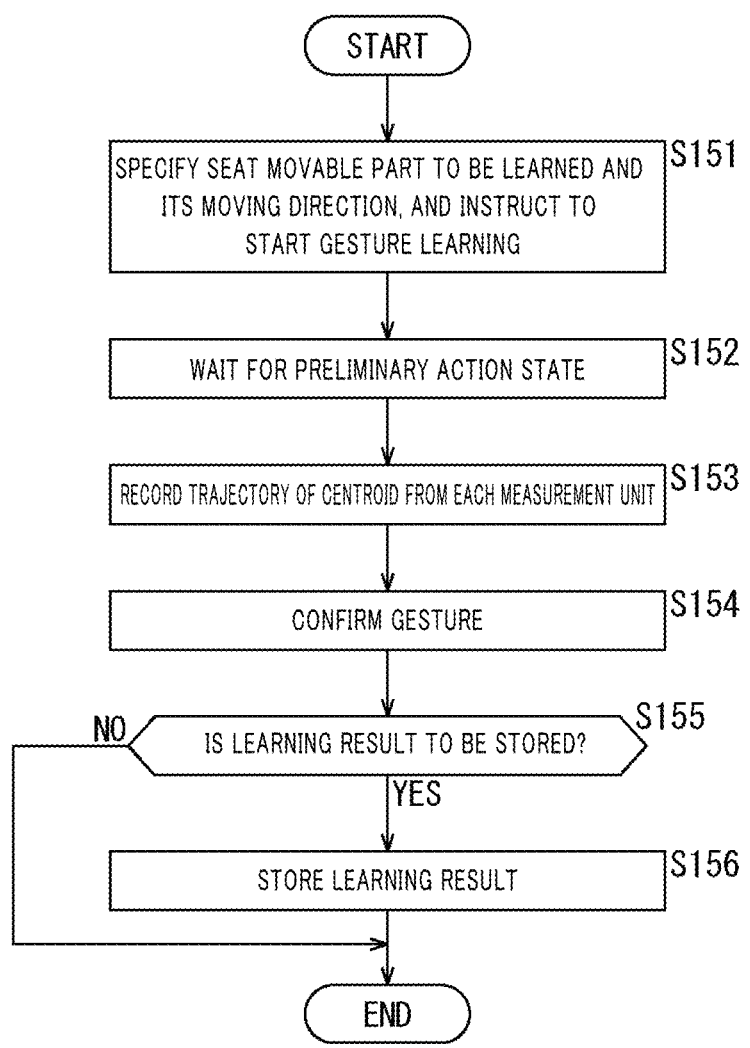
FIG. 30 is a flowchart illustrating gesture learning processing.

Gesture learning processing performed by the gesture input determination unit 17 will be described with reference to a flowchart illustrated in FIG. 30.

In step S151, the gesture input determination unit 17 specifies one or some of the movable parts of the seat 61 to be learned and their movable direction among the headrest part 62, the backrest part 63, the seat surface part 64, and the footrest part 65, and detects the reception of an occupant's instruction to start gesture learning.

In step S152, the gesture input determination unit 17 waits for the preliminary action waiting state in which the preliminary action determination conditions are satisfied as described with reference to the flowchart in FIG. 23. Then, when it is in the preliminary action waiting state, the processing proceeds to step S153.

Figure 27:
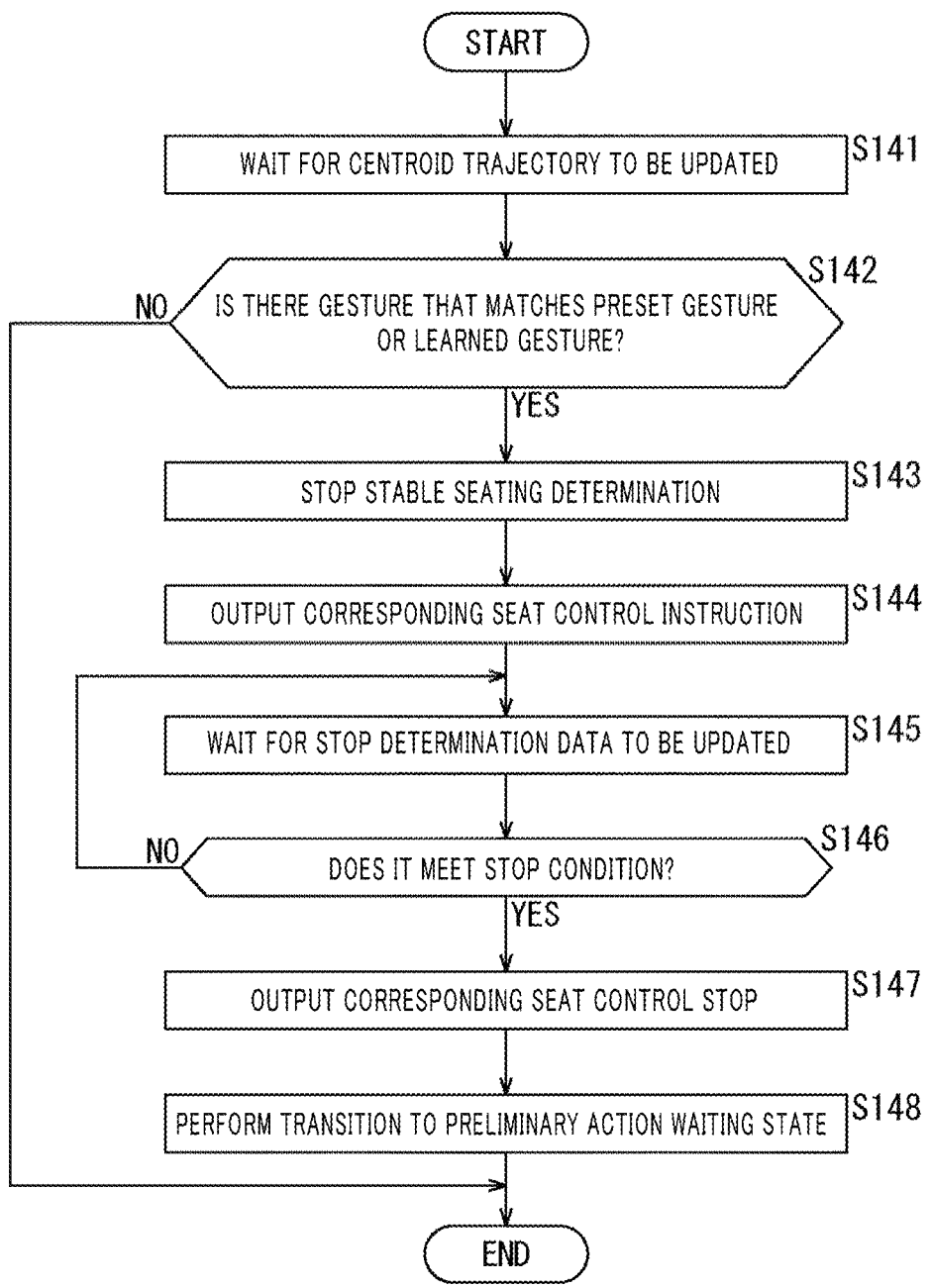
FIG. 27 is a flowchart illustrating gesture determination processing.

In step S153, the gesture input determination unit 17 acquires the pressure distribution data (i.e., changes in load distribution shape in the short-term section S and the long-term section L) as in step S141 of FIG. 27, and records the trajectory of the centroid according to the changes of the pressure distribution data.

In step S154, the gesture input determination unit 17 confirms the trajectory of the centroid acquired in step S153 as a gesture.

In step S155, according to whether a trajectory of the centroid that is likely to be a gesture is recorded as a result of the confirmation in step S154, the gesture input determination unit 17 determines whether or not to store that trajectory of the centroid as a learning result.

When it is determined in step S155 to store the learning result, the processing proceeds to step S156, and then the gesture input determination unit 17 stores the learning result.

On the other hand, when it is determined in step S155 not to store the learning result, or after the processing of step S156, the processing ends.

Performing the above-described gesture learning processing makes it possible to store any gesture other than the preset gestures and achieve the control of the operation outputs according to the gesture.

Figure 31:
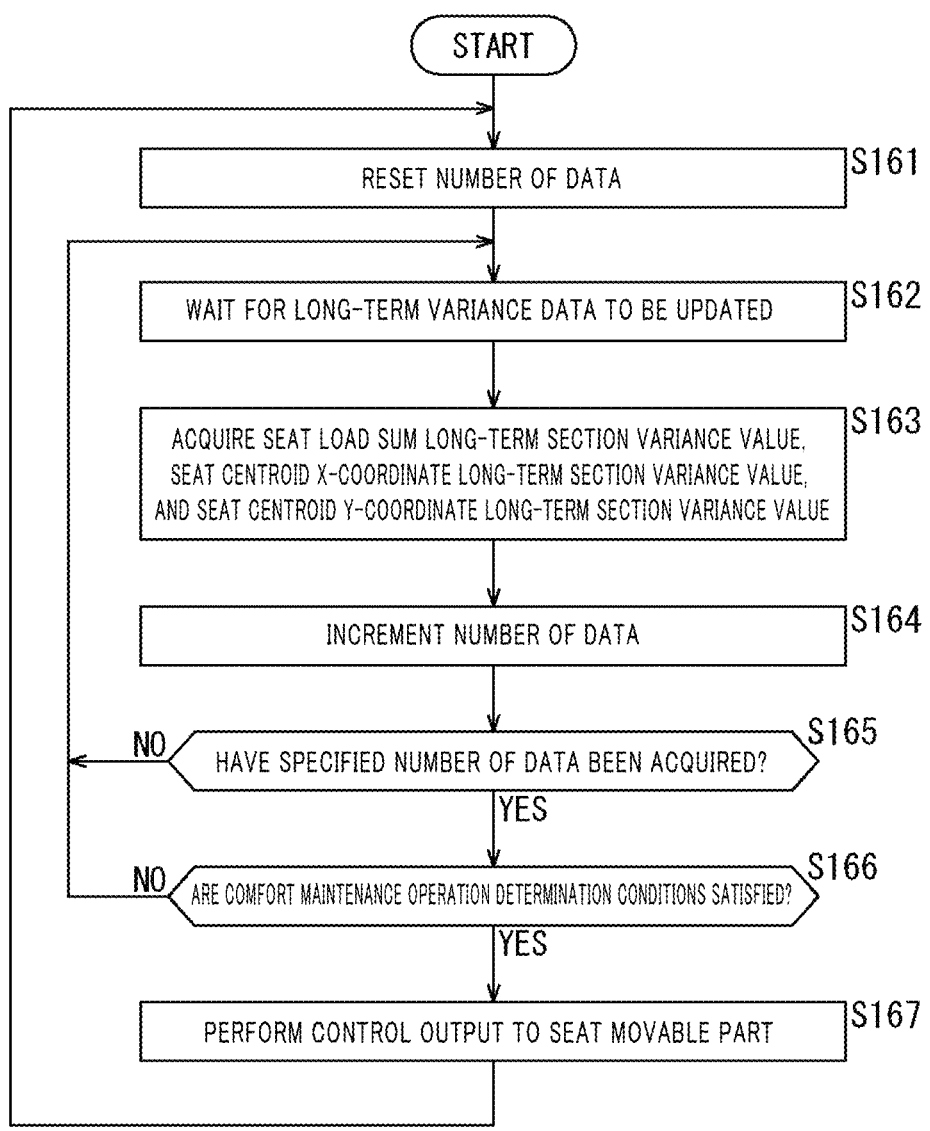
FIG. 31 is a flowchart illustrating comfort maintenance operation determination processing.

The comfort maintenance operation determination processing performed in the gesture disabled state illustrated in FIG. 17 or in the stable seating state illustrated in FIG. 18 will be described with reference to the flowchart illustrated in FIG. 31.

In step S161, the body load determination unit 18 resets the number of data (N=0)

In step S162, the body load determination unit 18 waits for the long-term variance value to be updated by the load change statistical processing unit 13 performing the processing of steps S22 to S24 of FIG. 14. Then, when the long-term variance value is supplied from the load change statistical processing unit 13 to the gesture input determination unit 17, the processing proceeds to step S163.

In step S163, the body load determination unit 18 acquires the seat load sum long-term section variance value LS2_Wsum_SE, the seat centroid x-coordinate long-term section variance value LS2_Cx_SE, and the seat centroid y-coordinate long-term section variance value LS2_Cy_SE from among the long-term variance values supplied from the load change statistical processing unit 13 in step S162.

In step S164, the body load determination unit 18 increments the number of data (N++).

In step S165, the body load determination unit 18 determines whether or not the specified number of data has been acquired. For example, when the specified number of data is 120, the body load determination unit 18 determines whether or not the number of data incremented in step S164 is 120 (N=120).

When the body load determination unit 18 determines in step S165 that the specified number of data has not been acquired, the processing returns to step S162, and when the body load determination unit 18 determines that the specified number of data has been acquired, the processing proceeds to step S166.

In step S166, the body load determination unit 18 uses determination parameters (predetermined specified values) to determine whether or not the seat load sum long-term section variance value LS2_Wsum_SE, the seat centroid x-coordinate long-term section variance value LS2_Cx_SE, and the seat centroid y-coordinate long-term section variance value LS2_Cy_SE satisfy comfort maintenance operation determination conditions.

For example, for all of the latest specified number of data (e.g., 120), when the seat load sum long-term section variance value LS2_Wsum_SE is smaller than a seat load sum determination parameter COND_K-COF_Wsum_SE, the seat centroid x-coordinate long-term section variance value LS2_Cx_SE is smaller than a seat centroid x-coordinate determination parameter COND_K-COF_Cx_SE, and the seat centroid y-coordinate long-term section variance value LS2_Cy_SE is smaller than a seat centroid y-coordinate determination parameter COND_K-COF_Cy_SE, the body load determination unit 18 determines that the comfort maintenance operation determination conditions are satisfied.

That is, when the following are all TRUE for all of the latest specified number of data:
LS2_Wsum_SE<COND_K-COF_Wsum_SE
LS2_Cx_SE<COND_K-COF_Cx_SE
LS2_Cy_SE<COND_K-COF_Cy_SE,
the body load determination unit 18 determines that the comfort maintenance operation determination conditions are satisfied.

When the body load determination unit 18 determines in step S166 that the comfort maintenance operation determination conditions are not satisfied, the processing returns to step S162, and when the body load determination unit 18 determines that the comfort maintenance operation determination conditions are satisfied, the processing proceeds to step S167.

In step S167, the body load determination unit 18 controls the operation outputs for the movable parts of the seat 61 so that the seat 61 is turned into a form that relieves the physical fatigue of the occupant. After the processing of step S167, the processing proceeds to step S161, and then the same processing is repeated.

<Configuration Example of Computer>

Next, the series of processing described above can be performed by hardware or software. In a case where the series of processing is performed by software, a program serving as software is installed on a general-purpose computer or the like.

Figure 32:
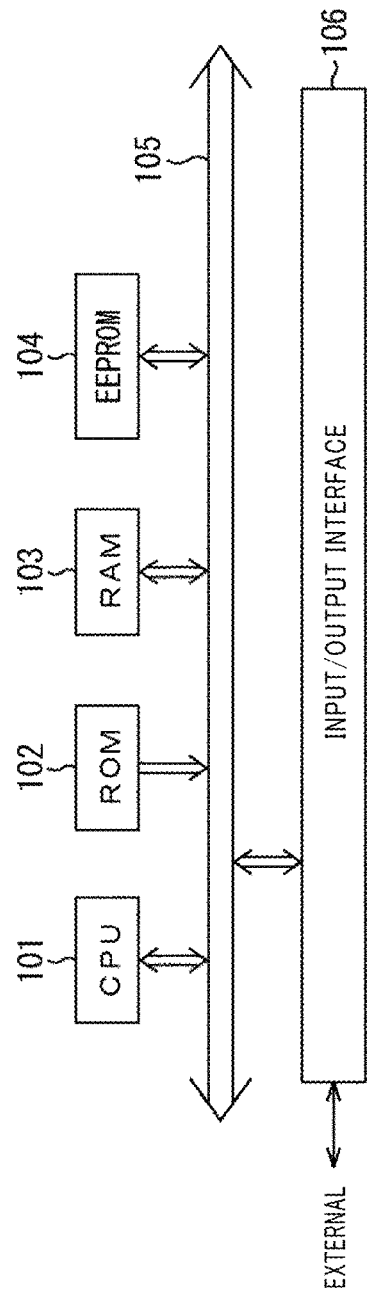
FIG. 32 is a block diagram illustrating a configuration example of one embodiment of a computer to which the present technique is applied.

FIG. 32 is a block diagram illustrating a configuration example of an embodiment of a computer on which a program for executing the series of processing described above is installed.

In the computer, a CPU (Central Processing Unit) 101, a ROM (Read Only Memory) 102, a RAM (Random Access Memory) 103, and an EEPROM (Electronically Erasable and Programmable Read Only Memory) 104 are connected to each other via a bus 105. An input/output interface 106 is further connected to the bus 105, and the input/output interface 106 is externally connected.

In the computer configured as described above, the CPU 101 loads the program stored in the ROM 102 and the EEPROM 104 into the RAM 103 via the bus 105, and executes the program, thereby performing the series of processing described above. The program to be executed by the computer (CPU 101) can be written in the ROM 102 in advance, or can be externally installed or updated on the EEPROM 104 via the input/output interface 106.

Here, in the present description, the processing performed by the computer according to the program does not necessarily have to be performed in time series in the order described as the flowchart. Specifically, the processing performed by the computer according to the program also includes steps of processing that are executed in parallel or individually (e.g., parallel processing or object processing).

Further, the program may be processed by one computer (processor) or may be processed by a plurality of computers in a distributed manner. Furthermore, the program may be transferred to a remote computer where it is executed.

Further, in the present description, the system means a set of a plurality of constituent elements (devices, modules (components), etc.), and it does not matter whether or not all the constituent elements are in the same housing. Therefore, a plurality of devices housed in separate housings and connected via a network, and one device housing a plurality of modules in one housing are both referred to as the systems.

Further, for example, the configuration described as one device (or processing unit) may be divided to be configured as a plurality of devices (or processing units). Conversely, the configurations described as a plurality of devices (or processing units) in the above description may be integrated to be configured as one device (or processing unit). Further, needless to say, it may be configured to include additional constituent element(s) other than the above configuration in each device (or each processing unit). Furthermore, if the configuration and operation of the entire system are substantially the same, part of the configuration of a certain device (or processing unit) may be included in the configuration of another device (or another processing unit).

In addition, for example, the present technique can be configured as cloud computing in which a plurality of devices share and jointly process one functionality via a network.

Further, for example, the above-described program can be executed in any device. In that case, the device may have a necessary function (function block or the like) so that necessary information can be obtained.

Further, for example, each step described in the above-described flowcharts can be executed by one device or shared by a plurality of devices. Furthermore, in a case where one step includes a plurality of steps of processing, the plurality of steps of processing included in the one step can be executed by one device or shared by a plurality of devices. In other words, the plurality of steps of processing included in the one step can be executed as processing of a plurality of steps. Conversely, the processing described as a plurality of steps can be collectively executed as one step.

Note that the program to be executed by the computer may be such that the steps of processing describing the program are executed in time series in the order described in the present description, or they are executed in parallel or individually at a necessary timing such as when a call is made. In other words, as long as no contradiction occurs, the steps of processing may be executed in an order different from the order described above. Furthermore, the steps of processing describing this program may be executed in parallel with the processing of another program, or may be executed in combination with the processing of another program.

Note that the present plurality of techniques described in the present description can be implemented independently as a single one unless a contradiction occurs. Needless to say, some of the present plurality of techniques can be implemented together. For example, part or all of the present technique described in any of the embodiments can be implemented in combination with part or all of the present techniques described in the other embodiments. Further, part or all of any of the present techniques described above can be implemented in combination with another technique not described above.

<Combination Examples of Configuration>

Note that the present techniques may also be configured as follows.

(1)

A control device including:
  a measurement unit that measures pressure distributions for a plurality of measurement ranges of a seat on which a user is seated, and time variations of the pressure distributions; and
  a control unit that controls operation of a device according to a measurement result from the measurement unit.

(2)

The control device according to (1), wherein the control unit controls operation of the seat according to a measurement result from the measurement unit.

(3)

The control device according to (2), further including a gesture input determination unit that determines that a behavior of the user is a gesture for a predetermined operation input according to a measurement result from the measurement unit,
  wherein the control unit controls operation of the seat according to the gesture of the user.

(4)

The control device according to (3), wherein the gesture input determination unit determines whether the behavior of the user is a gesture intended to be the operation input or a posture change not intended to be the operation input.

(5)

The control device according to (4), wherein the gesture input determination unit determines whether the behavior of the user is a gesture intended to be the operation input or a posture change not intended to be the operation input, according to a measurement result measured by the measurement unit following a predetermined preliminary action.

(6)

The control device according to (4), wherein the gesture input determination unit determines whether the behavior of the user is a gesture intended to be the operation input or a posture change not intended to be the operation input, according to a measurement result measured by the measurement unit following a predetermined preliminary action.

(7)

The control device according to any one of (1) to (6), wherein the control unit controls operation of an entertainment device in an interior of a vehicle equipped with the seat according to a measurement result from the measurement unit.

(8)

The control device according to any one of (1) to (7), wherein the control unit controls operation of an environmental control device in an interior of a vehicle equipped with the seat according to a measurement result from the measurement unit.

(9)

The control device according to any one of (2) to (8), further including a determination unit that determines whether the user experiences physical fatigue according to a measurement result from the measurement unit, wherein the control unit controls operation of the seat based on a determination result from the determination unit.

(10)

The control device according to any one of (2) to (9), further including an estimation unit that estimates a state of the user based on biological information of the user,
  wherein the control unit controls operation of the seat based on an estimation result from the estimation unit.

(11)

The control device according to any one of (4) to (10), wherein the gesture input determination unit determines whether the behavior of the user is a gesture intended to be the operation input or a posture change not intended to be the operation input according to whether it is caused by a time variation of pressure distribution based on a vibration of a vehicle equipped with the seat.

(12)

A control method performed by a control device for performing control, the control method including:
  measuring pressure distributions for a plurality of measurement ranges of a seat on which a user is seated, and time variations of the pressure distributions; and controlling a device according to a measurement result from the measuring.

(13)

A program for causing a computer of a control device for performing control to execute:
  measuring pressure distributions for a plurality of measurement ranges of a seat on which a user is seated, and time variations of the pressure distributions; and controlling a device according to a measurement result from the measuring.

(14)

A mobile object provided with a seat on which a user is seated, the mobile object including:
  a measurement unit that measures pressure distributions for a plurality of measurement ranges of the seat, and time variations of the pressure distributions; and
  a control unit that controls operation of a device according to a measurement result from the measurement unit.

Note that embodiments of the present invention are not limited to the above-described embodiments, and various modifications can be made without departing from the spirit of the present disclosure. Further, the advantageous effects described in the present description are merely examples and are not limited, and there may be provided other advantageous effects.

REFERENCE SIGNS LIST

11 Control processor
12 Pressure distribution measurement unit
13 Load change statistical processing unit
14 Body measurement unit
15 Heartbeat measurement unit
16 Respiration measurement unit
17 Gesture input determination unit
18 Body load determination unit
19 Mental and physical condition estimation unit 20 Vehicle body motion measurement unit
21 Device operation unit
22 Seat control unit
23 User notification unit
24 Driving function notification unit
31 Head part pressure distribution measurement unit
32 Back part pressure distribution measurement unit
33 Seating part pressure distribution measurement unit
34 Leg part pressure distribution measurement unit
35 Bottom part pressure distribution measurement unit
51 Vehicle
61 Seat
62 Headrest part
63 Backrest part
64 Seat surface part
65 Footrest part
66 Floor

The invention claimed is:

1. A control device comprising:
circuitry configured to
obtain pressure distribution data by measuring pressure distributions for a plurality of measurement ranges of a seat of a vehicle on which a user is seated, and time variations of the pressure distributions,
perform statistical processing on the pressure distribution data to obtain statistically processed pressure distribution data of load changes during a predetermined period of time while the user is seated on the seat, according to behavior of the user,
determine whether the user experiences physical fatigue according to the statistically processed pressure distribution data, and
control operation of a device of the vehicle based on a result of determination that the user experiences the physical fatigue.

2. The control device according to claim 1,
wherein the circuitry is configured to
determine that the behavior of the user is a gesture of the user for a predetermined operation input based on the statistically processed pressure distribution data, and
control operation of the device of the vehicle based on the gesture of the user.

3. The control device according to claim 2,
wherein the circuitry is configured to calculate an average value and a variance value of the pressure distribution data in a short-time section and in a long term section, respectively, as the statistically processed pressure distribution data, and
wherein the circuitry is configured to perform preliminary action determination processing to determine that a preliminary action for transition to a gesture waiting state is performed based on the variance value of the pressure distribution data in the short-time section.

4. The control device according to claim 3, wherein the circuitry is configured to determine whether the behavior of the user is the gesture intended to be the operation input or a posture change not intended to be the operation input.

5. The control device according to claim 4, wherein the circuitry is configured to determine whether the behavior of the user is the gesture intended to be the operation input or the posture change not intended to be the operation input, according to the statistically processed pressure distribution data obtained following a predetermined preliminary action.

6. The control device according to claim 4, wherein the circuitry is configured to determine whether the behavior of the user is the gesture intended to be the operation input or the posture change not intended to be the operation input, according to the statistically processed pressure distribution data obtained following the predetermined operation input.

7. The control device according to claim 2, wherein the circuitry is configured to control operation of an entertainment device in an interior of the vehicle equipped with the seat according to the gesture of the user.

8. The control device according to claim 2, wherein the circuitry is configured to control operation of an environmental control device in an interior of the vehicle equipped with the seat according to the gesture of the user.

9. The control device according to claim 2, wherein the circuitry is configured to control operation of the seat based on the result of determination that the user experiences the physical fatigue.

10. The control device according to claim 2, wherein the circuitry is configured to estimate a state of the user based on biological information of the user, wherein the circuitry is configured to control operation of the device based on an estimation result.

11. The control device according to claim 4, wherein the circuitry is configured to determine whether the behavior of the user is a gesture intended to be the operation input or a posture change not intended to be the operation input according to whether it is caused by a time variation of pressure distribution based on a vibration of the vehicle equipped with the seat.

12. A control method performed by a control device for performing control, the control method including:
obtaining pressure distribution data by measuring pressure distributions for a plurality of measurement ranges of a seat of a vehicle on which a user is seated, and time variations of the pressure distributions;
performing statistical processing on the pressure distribution data to obtain statistically processed pressure distribution data of load changes during a predetermined period of time while the user is seated on the seat, according to behavior of the user;
determining whether the user experiences physical fatigue according to the statistically processed pressure distribution data; and
controlling operation of a device of the vehicle based on a result of determination that the user experiences the physical fatigue.

13. A non-transitory computer-readable storage medium including computer executable instructions, wherein the instructions, when executed by a control device, cause the control device to perform a method, the method comprising
obtaining pressure distribution data by measuring pressure distributions for a plurality of measurement ranges of a seat of a vehicle on which a user is seated, and time variations of the pressure distributions;
performing statistical processing on the pressure distribution data to obtain statistically processed pressure distribution data of load changes during a predetermined period of time while the user is seated on the seat, according to behavior of the user;
determining whether the user experiences physical fatigue according to the statistically processed pressure distribution data; and
controlling operation of a device of the vehicle based on a result of determination that the user experiences the physical fatigue.

14. A mobile object comprising:

a seat on which a user is seated; and circuitry configured to obtain pressure distribution data by measuring pressure distributions for a plurality of measurement ranges of the seat, and time variations of the pressure distributions, perform statistical processing on the pressure distribution data to obtain statistically processed pressure distribution data of load changes during a predetermined period of time while the user is seated on the seat, according to behavior of the user, determine whether the user experiences physical fatigue according to the statistically processed pressure distribution data, and control operation of a device of the mobile object based on a result of determination that the user experiences the physical fatigue.

15. The control device according to claim 1, wherein the statistically processed pressure distribution data includes at least one of a variance value of sum of seat load in a long-term section, a variance value of seat centroid in x-coordinate in the long-term section, and a variance value of seat centroid in y-coordinate in the long-term section, wherein the circuitry is configured to determine whether the user experiences physical fatigue based on comparison of at least one of the variance values of the statistically processed pressure distribution data with a predetermined parameter.

16. The control device according to claim 9, wherein the circuitry is configured to control operation of the seat of the vehicle based on the result of determination so that the seat is turned into a form that relieves the physical fatigue of the user.

17. The control device according to claim 16, wherein the circuitry is configured to adjust reclining of the seat as the operation of the seat of the vehicle.

* * * * *